United States Patent
Dustin et al.

(10) Patent No.: US 9,726,586 B2
(45) Date of Patent: Aug. 8, 2017

(54) STRENGTH TESTING OF A FLATWISE MATERIAL COUPON

(71) Applicant: The Boeing Company, Chicago, IL (US)

(72) Inventors: Joshua Shane Dustin, Maple Valley, CA (US); Jack J. Esposito, Auburn, WA (US); Alan W. Baker, Sammamish, WA (US)

(73) Assignee: The Boeing Company, Chicago, IL (US)

( * ) Notice: Subject to any disclaimer, the term of this patent is extended or adjusted under 35 U.S.C. 154(b) by 322 days.

(21) Appl. No.: 14/326,646

(22) Filed: Jul. 9, 2014

(65) Prior Publication Data
US 2016/0011089 A1    Jan. 14, 2016

(51) Int. Cl.
*G01N 3/08* (2006.01)
*B23B 51/04* (2006.01)

(52) U.S. Cl.
CPC ............. *G01N 3/08* (2013.01); *B23B 51/042* (2013.01); *B23B 2226/31* (2013.01); *B23B 2228/10* (2013.01); *B23B 2228/12* (2013.01); *B23B 2251/14* (2013.01); *B23B 2260/072* (2013.01); *G01N 2203/027* (2013.01); *G01N 2203/0262* (2013.01); *G01N 2203/0266* (2013.01); *G01N 2203/0274* (2013.01); *G01N 2203/0298* (2013.01); *Y10T 428/15* (2015.01)

(58) Field of Classification Search
CPC ..... G01N 2203/027; G01N 2203/0274; G01N 2203/0266; G01N 2203/0298; G01N 3/08
USPC ............................................... 428/43; 73/826
See application file for complete search history.

(56) References Cited

U.S. PATENT DOCUMENTS

| | | | | |
|---|---|---|---|---|
| 3,765,230 A | * | 10/1973 | Bohm | B23C 1/20 73/767 |
| 4,032,679 A | * | 6/1977 | Aoyagi | C09J 7/02 283/101 |
| 2014/0202256 A1 | * | 7/2014 | DeTeresa | G01M 5/005 73/788 |
| 2015/0308932 A1 | * | 10/2015 | Whittington | G01N 3/062 73/760 |
| 2016/0103047 A1 | * | 4/2016 | Liu | G01N 3/08 73/826 |

OTHER PUBLICATIONS

"Composite Material", Wikipedia, Retrieved from the Internet: <http://en.wikipedia.org/wiki/Composite_material>, Accessed on Jun. 10, 2014, 13 pgs.
"Drill bit", Wikipedia, Retrieved from the Internet: <http://en.wikipedia.org/wiki/Drill_bit>, Accessed on Jun. 10, 2014, 21 pgs.
(Continued)

*Primary Examiner* — William P Watkins, III
(74) *Attorney, Agent, or Firm* — Kwan & Olynick LLP

(57) ABSTRACT

One example of the present disclosure relates to a coupon. The coupon includes a first surface with a first circular channel and a second surface opposite and parallel to the first surface. The second surface is spaced a distance D0 from the first surface and includes a second circular channel concentric with the first circular channel. The coupon also includes a toroidal portion between the first circular channel and the second circular channel. The toroidal portion includes a rectangular sectional portion.

20 Claims, 14 Drawing Sheets

(56) References Cited

OTHER PUBLICATIONS

"Hole saw", Wikipedia, Retrieved from the Internet: <http://en.wikipedia.org/wiki/Hole_saw>, Accessed on Jun. 10, 2014, 3 pgs.
"Kerf", Wiktionary, Retrieved from the Internet: <http://en.wiktionary.org/wiki/kerf>, Accessed on Jun. 10, 2014, 2 pgs.
"Lamination", Wikipedia, Retrieved from the Internet: <http://en.wikipedia.org/wiki/Lamination>, Accessed on Jun. 10, 2014, 3 pgs.
"More about CNC Milling", Retrieved from the Internet: <http://www.thomasnet.com/about/cnc-milling-51276103.html>, Accessed on Jun. 10, 2014, 2 pgs.

* cited by examiner

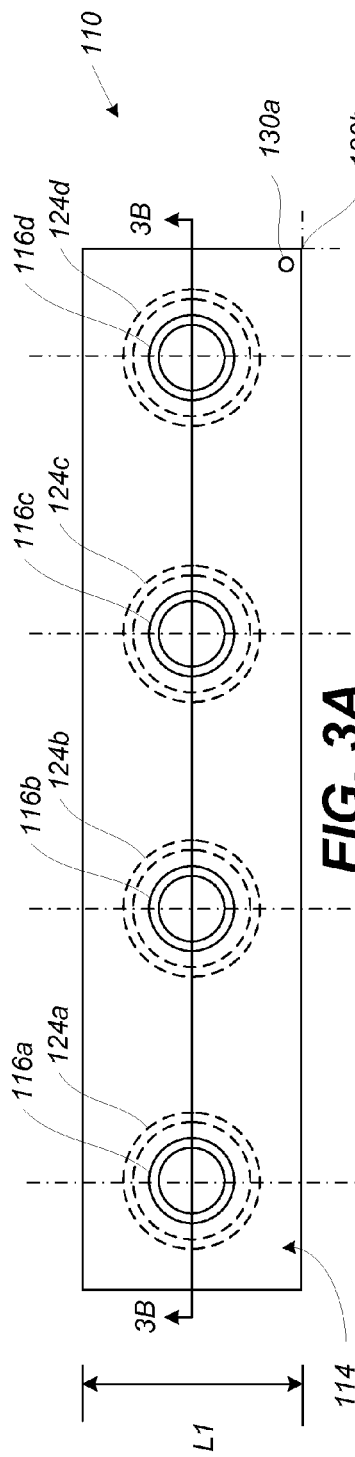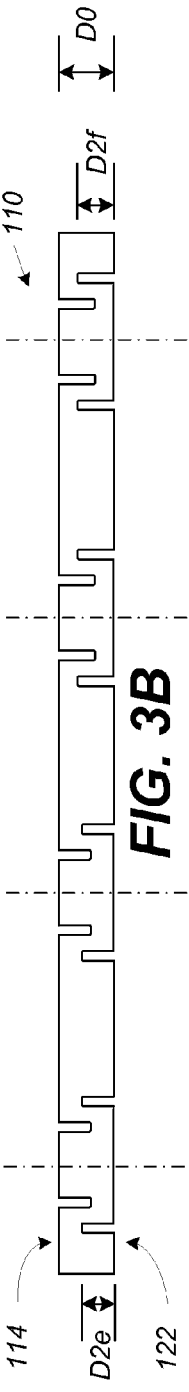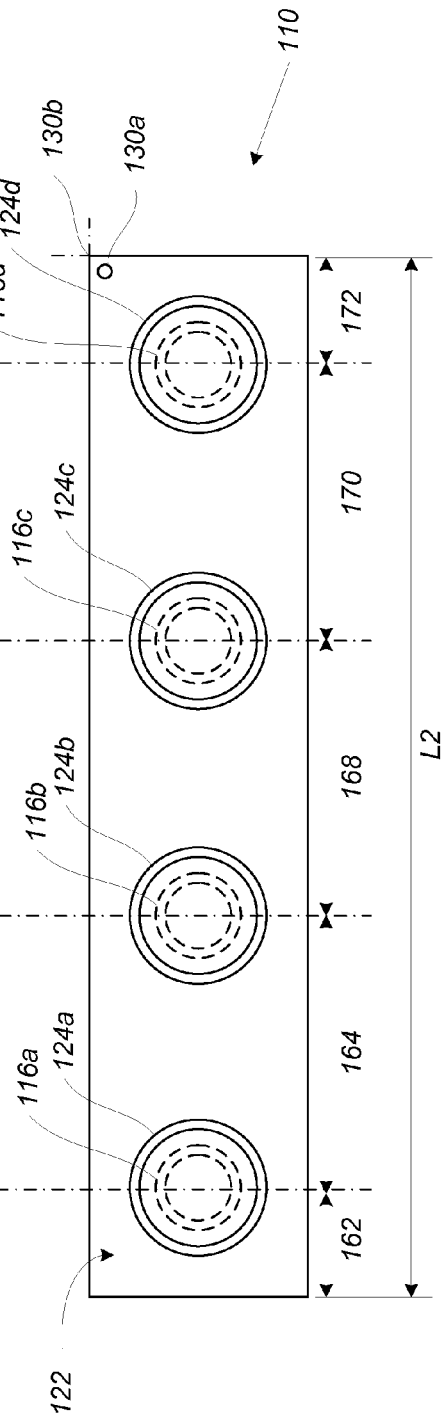

STRENGTH TESTING OF A FLATWISE MATERIAL COUPON

BACKGROUND

Determining properties of materials, such as composites, commonly includes measuring tensile and/or compressive strength thereof. To minimize undesirable stresses, traditional test methods often require adhesive bonding of test coupons to metal load blocks before applying loads via the metal load blocks. Because conventional bonding processes require the pieces being bonded to be dry, such bonding must be done with dry test coupons.

However, it is sometimes desirable to measure the strength of test coupons under environmental conditions such as high moisture or elevated temperatures. Because bonding of metal load blocks requires the test coupons to be dry, test coupons previously exposed to moisture cannot be tested. If the metal load blocks are adhered to a test coupon before the test coupon is exposed to environmental conditions, the metal load blocks will cover and block the test coupon from exposure to the environmental conditions. Additionally, when testing is performed at elevated temperatures and/or in high moisture environments, the adhesive bonds may weaken and prematurely fail, negatively affecting measurement accuracy. Accordingly, traditional testing techniques and mechanisms do not allow testing of composites under varied environmental conditions. In addition, bonding operations increase time and cost of the testing procedures.

SUMMARY

Accordingly, apparatus and method, intended to address the above-identified concerns, could find utility.

One example of the present disclosure relates to a coupon. The coupon includes a first surface with a first circular channel and a second surface opposite and parallel to the first surface. The second surface is spaced a distance $D0$ from the first surface and includes a second circular channel concentric with the first circular channel. The coupon also includes a toroidal portion between the first circular channel and the second circular channel. The toroidal portion includes a rectangular sectional portion.

One example of the present disclosure relates to a machining apparatus. The machining apparatus includes a first hole saw having a first longitudinal symmetry axis, a first shank, and a first cylindrical saw blade coupled to the first shank. The first cylindrical saw blade includes a first diameter, a length $L3$ along the first longitudinal symmetry axis, and at least one first slot including a length $L4$ parallel to the first longitudinal symmetry axis. The length $L4$ is less than the length $L3$.

One example of the present disclosure relates to a method of making a coupon from a material blank. The material blank includes a first surface on a first side of the material blank and a second surface opposite and parallel to the first surface on a second side of the material blank. The second surface is spaced a distance $D0$ from the first surface. The method includes forming a first circular channel in the material blank from the first side, such that the first circular channel is perpendicular to the first surface and includes an inner radius $R1b$, an outer radius $R1a$, and a depth $D1$. The depth $D1$ is less than the distance $D0$. The method of making a coupon from a material blank includes forming a second circular channel in the material blank from the second side, such that the second circular channel is perpendicular to the second surface and concentric with the first circular channel. The second circular channel includes a depth $D2$, an inner radius $R2b$, and an outer radius $R2a$. The depth $D2$ is less than the distance $D0$. A sum of the depth $D1$ and the depth $D2$ is greater than the distance $D0$. The inner radius $R2b$ is greater than the outer radius $R1a$.

One example of the present disclosure relates to a method of testing a coupon. The coupon includes a first surface including a first circular channel and a second surface opposite and parallel to the first surface. The second surface is spaced a distance $D0$ from the first surface and includes a second circular channel that is concentric with the first circular channel. A toroidal portion is located between the first circular channel and the second circular channel, which includes a rectangular sectional portion. The first surface includes a first inner region located within an inner radius $R1b$ of the first circular channel and a first outer region located outside an outer radius $R1a$ of the first circular channel. The second surface includes a second inner region located within an inner radius $R2b$ of the second circular channel and a second outer region located outside an outer radius $R2a$ of the second circular channel. The outer radius $R1a$ is less than the inner radius $R2b$.

The method of testing the coupon includes exerting a stress on the toroidal portion of the coupon and measuring deformation of the toroidal portion responsive to the stress.

BRIEF DESCRIPTION OF THE DRAWINGS

Figure 1:
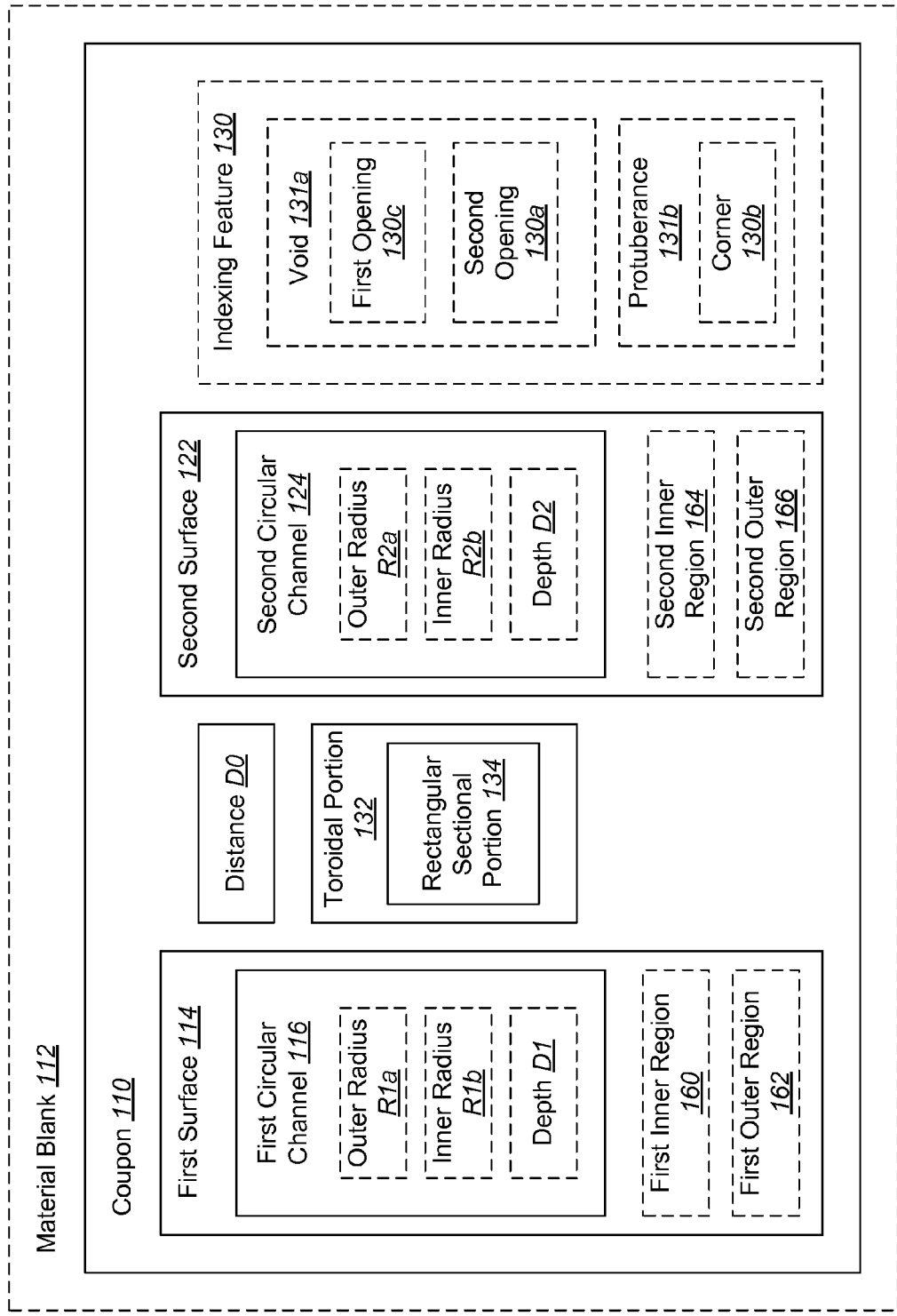
Figure 2A:
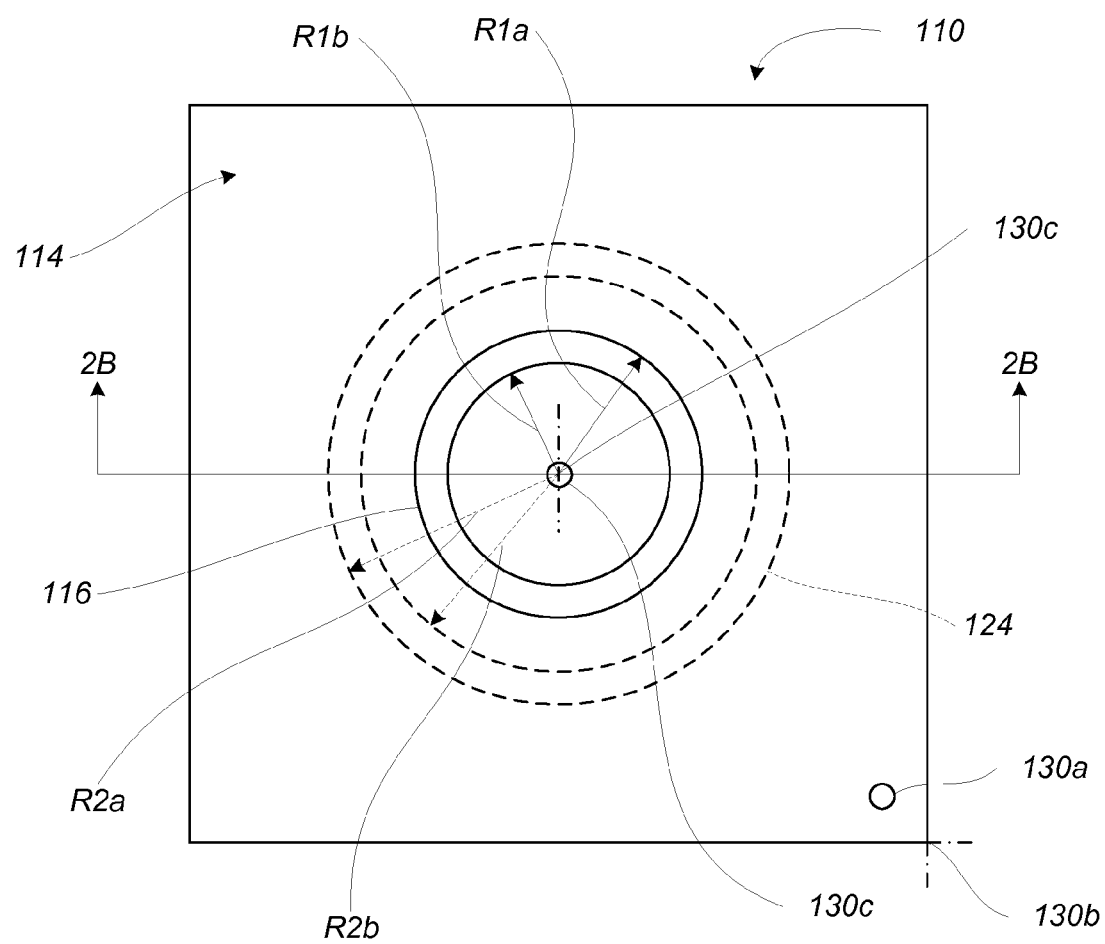
Figure 2B:
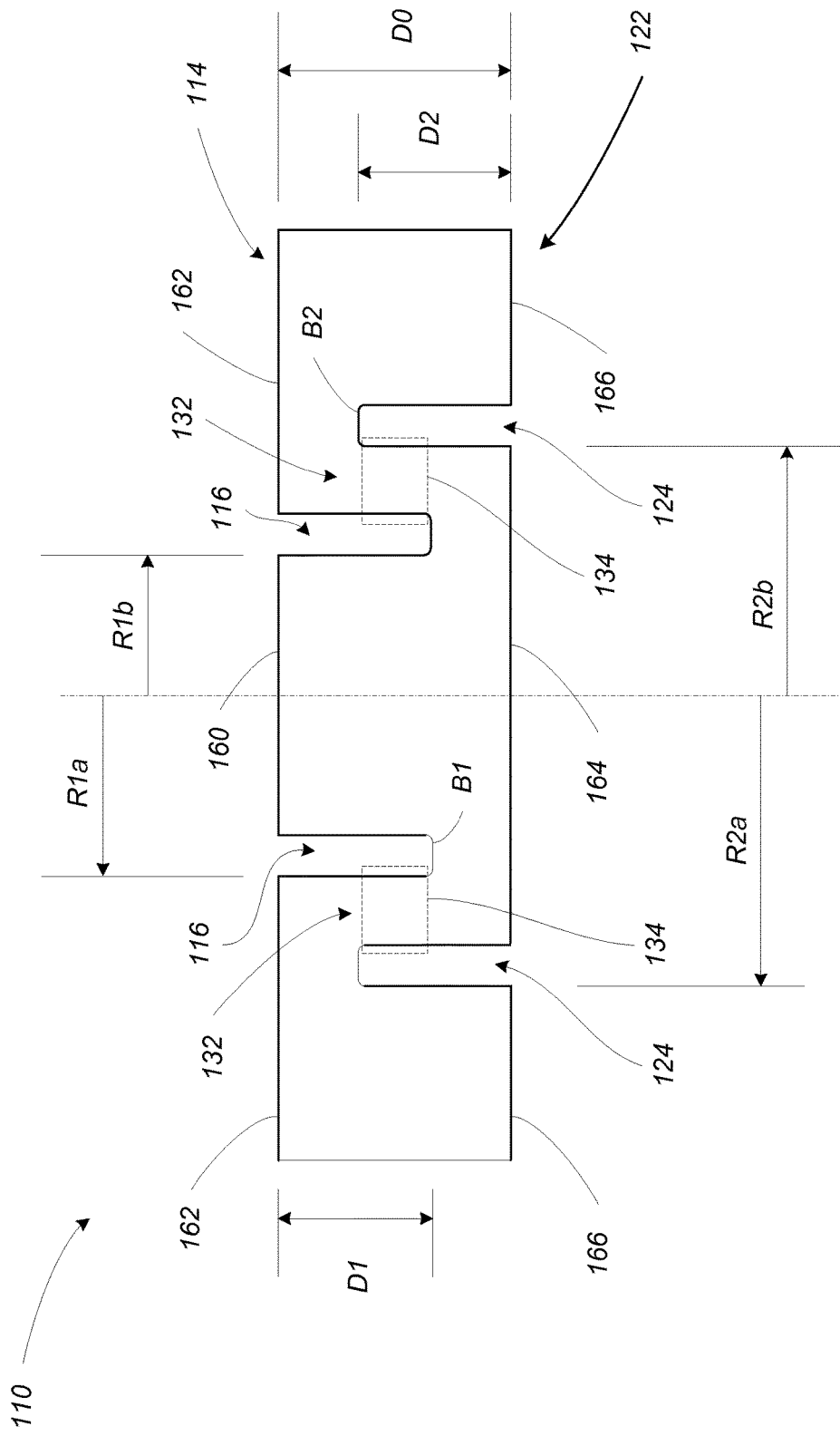
Figure 2C:
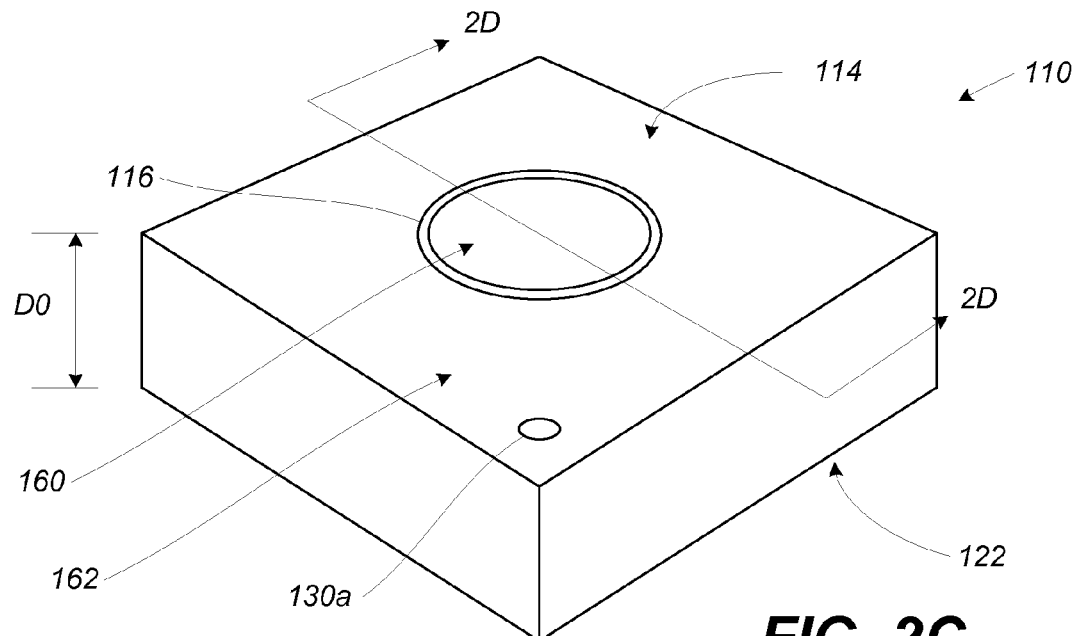
Figure 2D:
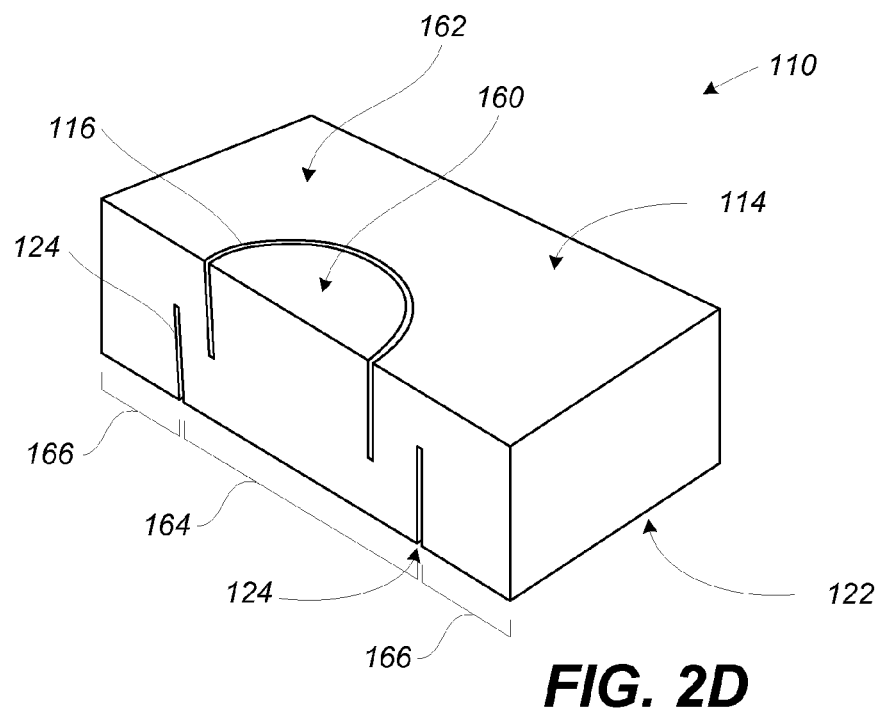
Figure 4:
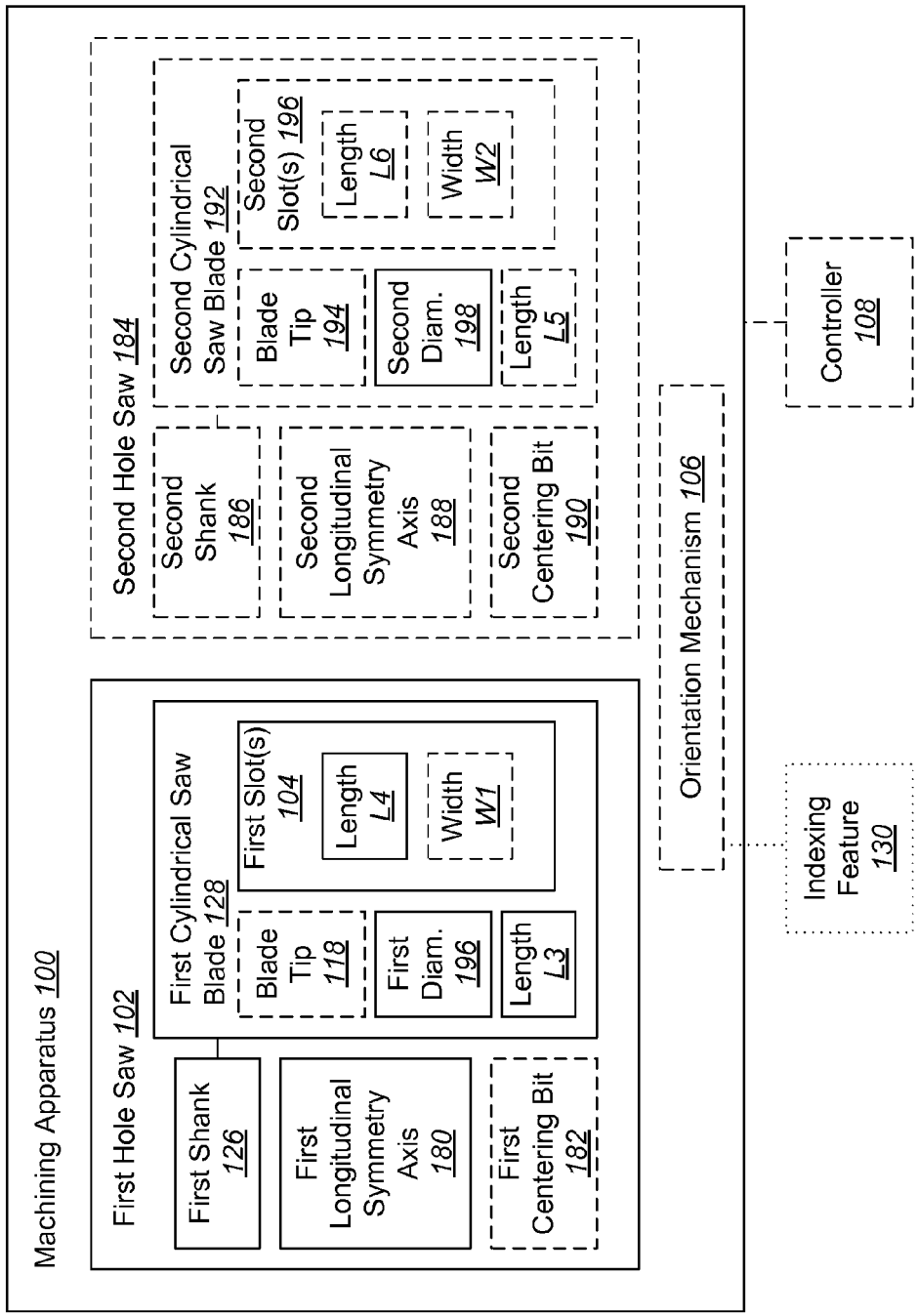
Figure 5B:
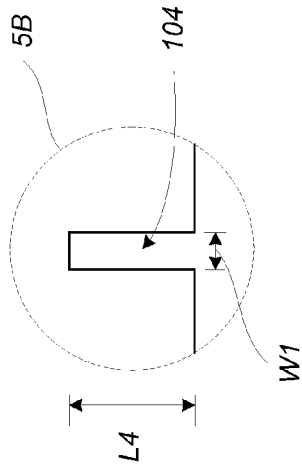
Figure 5C:
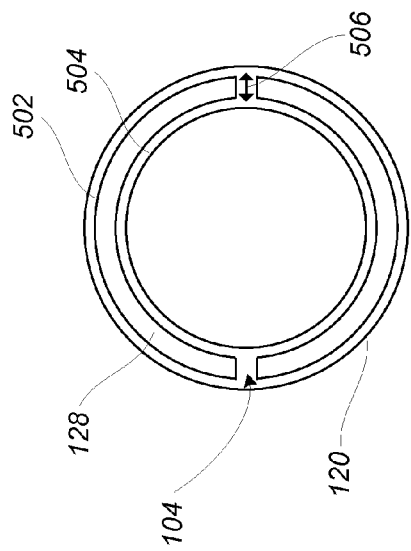
Figure 5A:
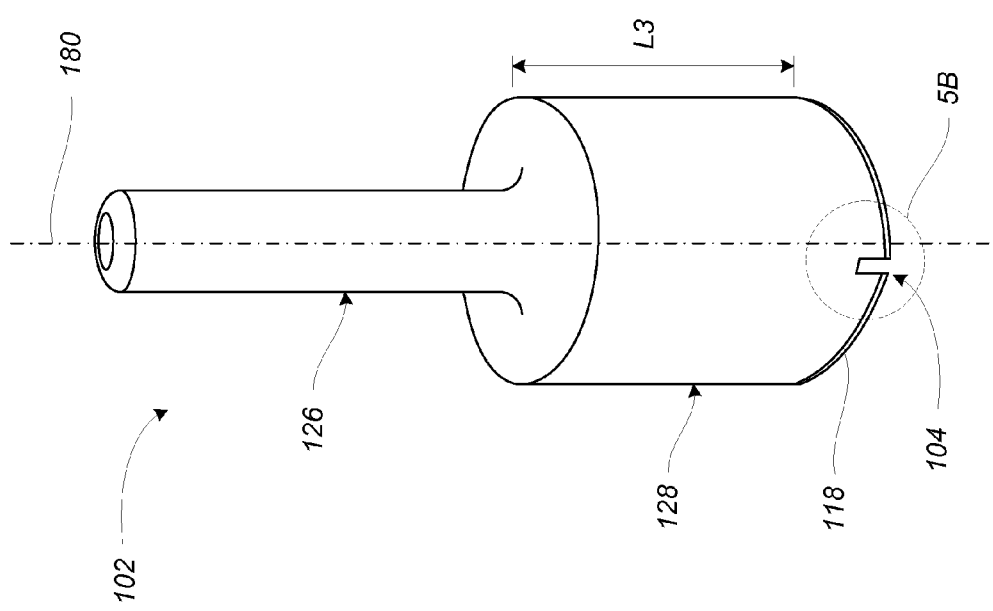
Figure 6:
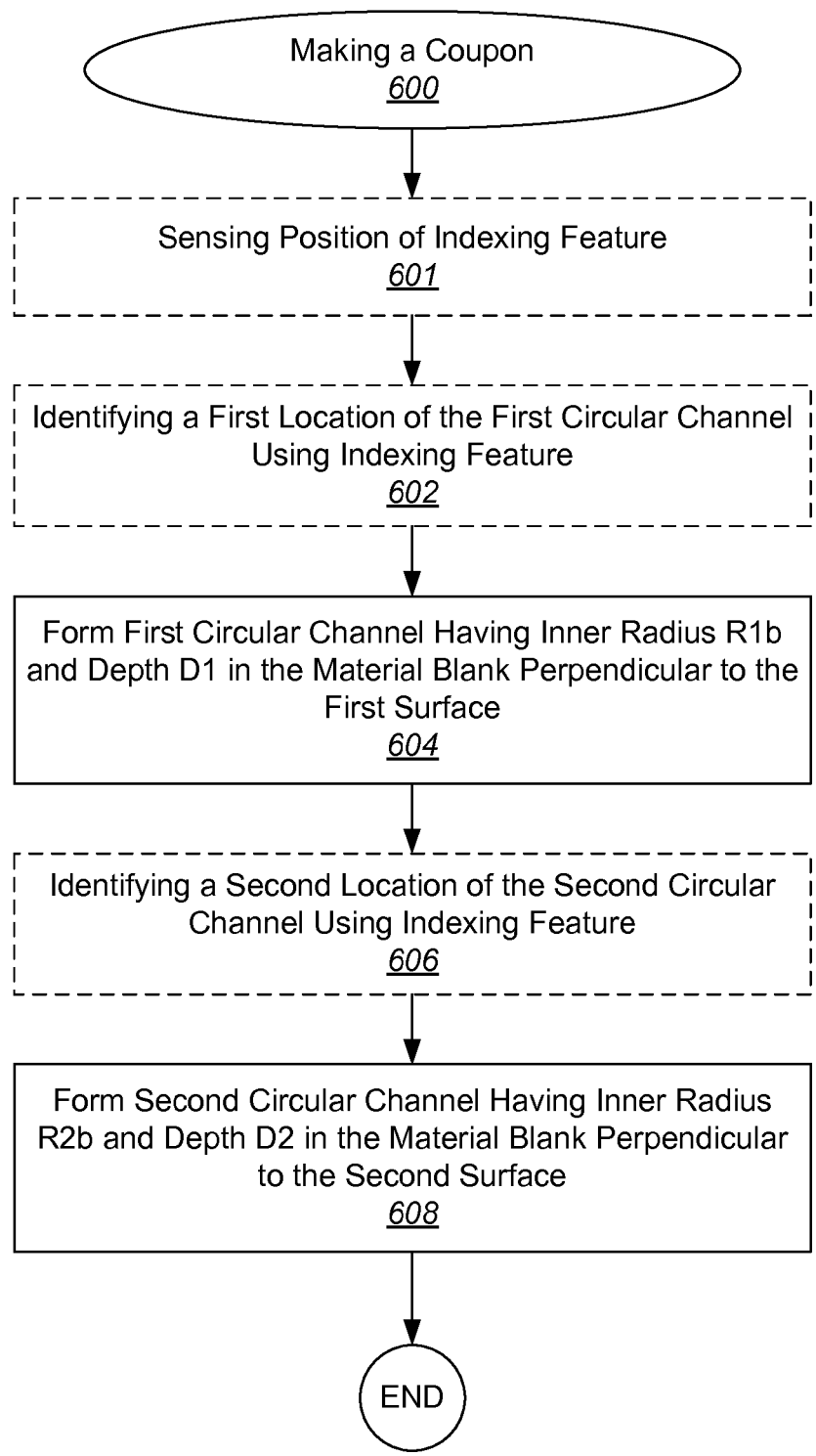
Figure 7:
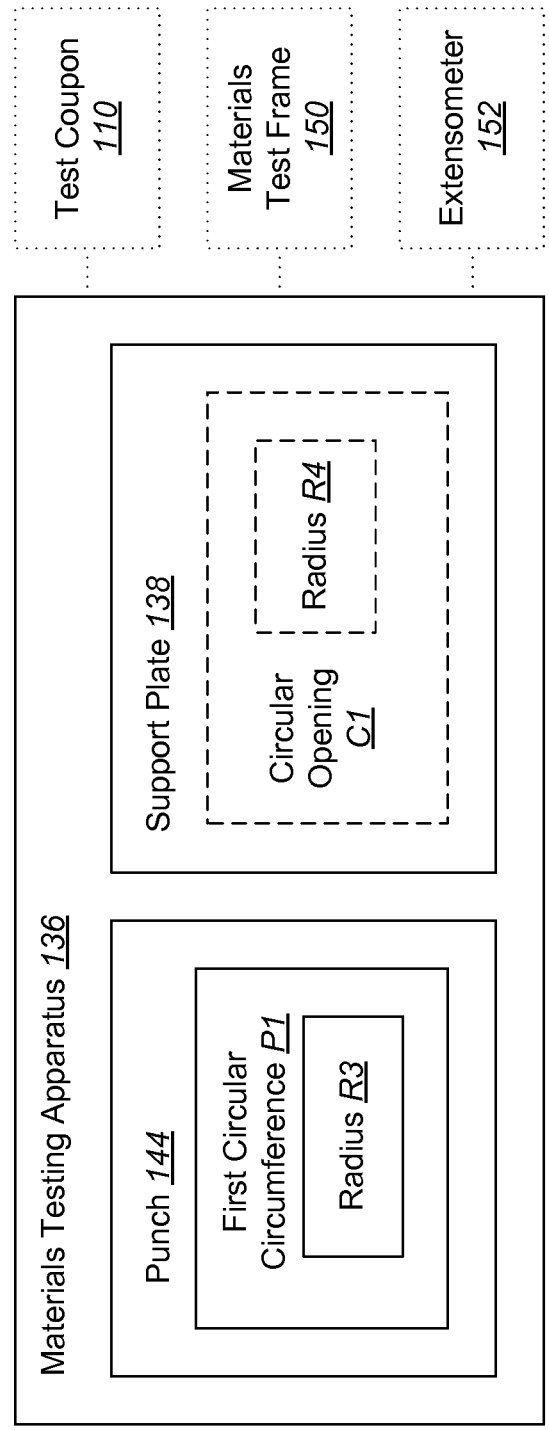
Figure 8A:
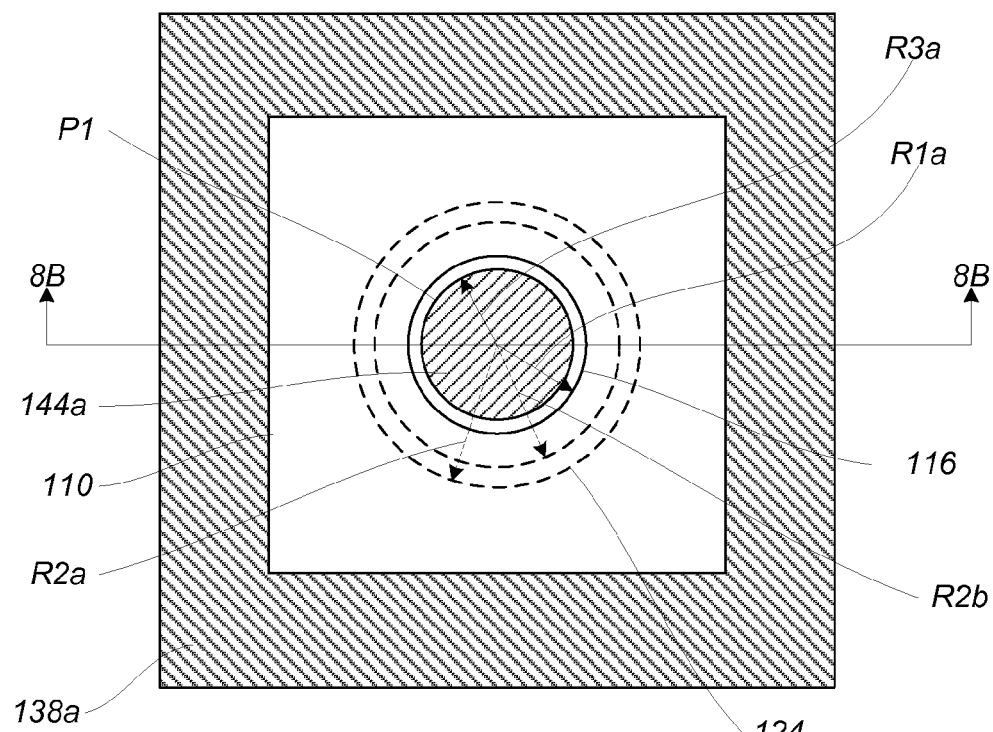
Figure 8B:
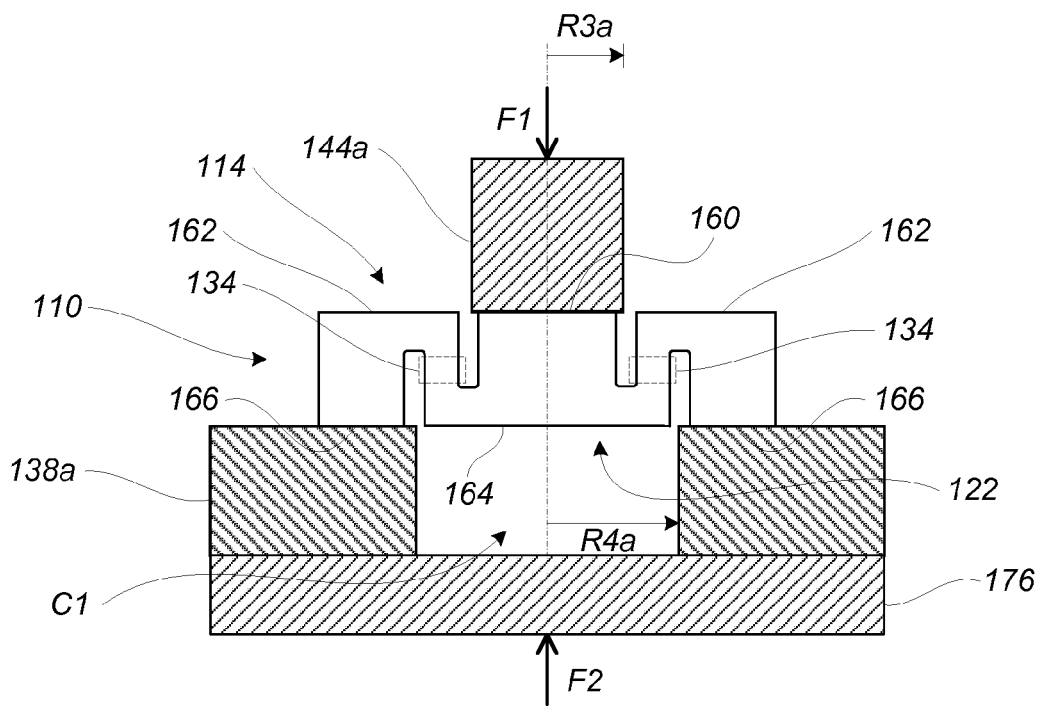
Figure 9A:
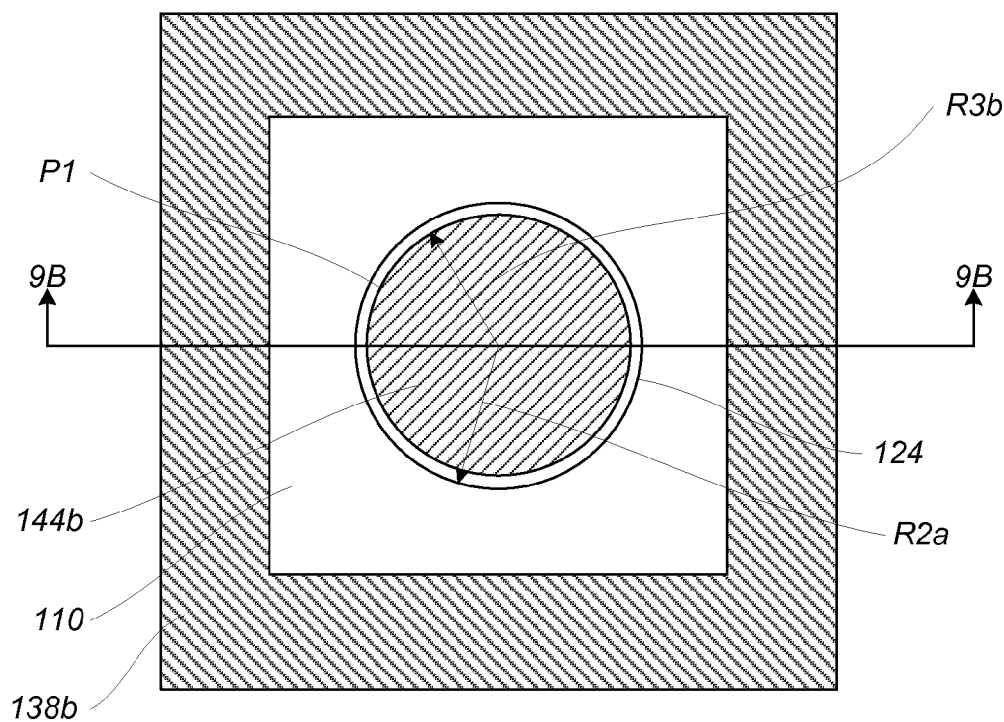
Figure 9B:
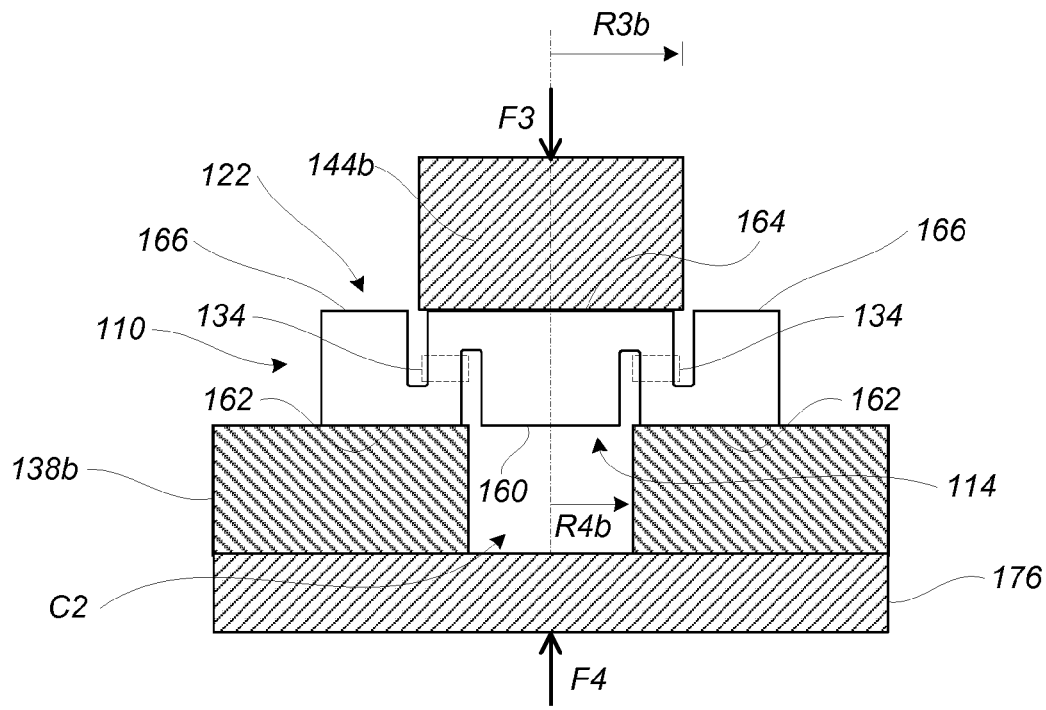
Figure 10:
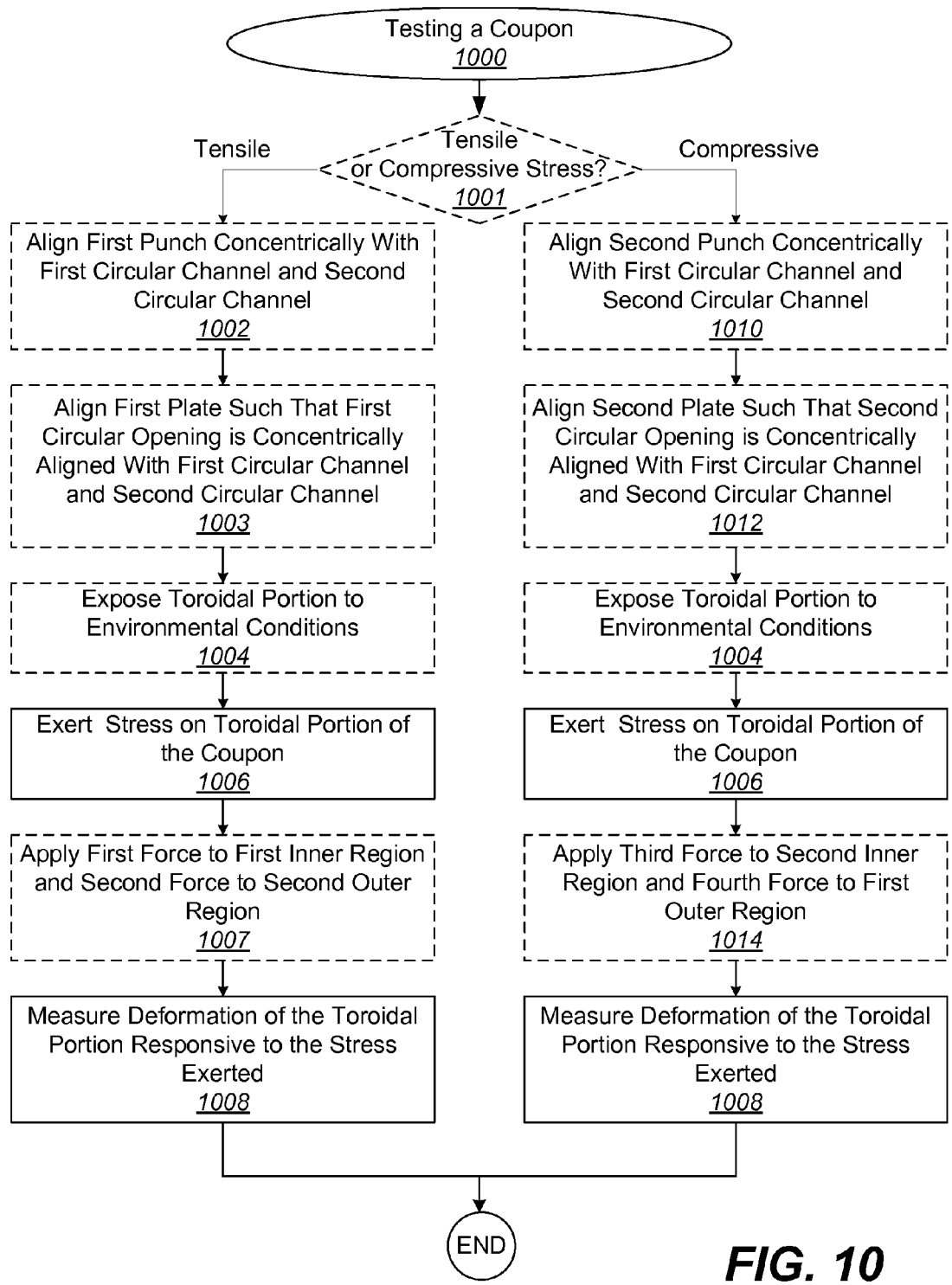

Having thus described examples of the disclosure in general terms, reference will now be made to the accompanying drawings, which are not necessarily drawn to scale, and wherein like reference characters designate the same or similar parts throughout the several views, and wherein:

FIG. 1 is a block diagram of a coupon made from a material blank, according to one aspect of the present disclosure;

FIG. 2A is a schematic view of the coupon of FIG. 1, according to one aspect of the disclosure;

FIG. 2B is a schematic cross-sectional view of the coupon of FIG. 1, according to one aspect of the disclosure;

FIG. 2C is a schematic perspective view of the coupon of FIG. 1, according to one aspect of the disclosure;

FIG. 2D is a schematic sectional perspective view of the coupon of FIG. 1, according one aspect of the disclosure;

FIG. 3A is a schematic top plan view of a material blank having multiple coupons, according to one aspect of the disclosure;

FIG. 3B is a schematic cross-sectional view of the material blank of FIG. 3A, according to one aspect of the disclosure;

FIG. 3C is a schematic bottom plan view of the material blank of FIG. 3A, according to one aspect of the disclosure;

FIG. 4 is a block diagram of a machining apparatus, according to one aspect of the disclosure;

FIG. 5A is a schematic perspective view of a hole saw of the machining apparatus of FIG. 4, according to one aspect of the disclosure;

FIG. 5B is a schematic detail view of the hole saw of FIG. 5A, according to one aspect of the disclosure;

FIG. 5C is a schematic cross-sectional view of the hole saw of FIG. 5A located within a channel, according to one aspect of the disclosure;

FIG. 6 is a block diagram of a method of making a coupon, according to one aspect of the disclosure;

FIG. 7 is a block diagram of a materials testing apparatus, according to one aspect of the disclosure;

FIG. 8A is a schematic plan view of the materials testing apparatus of FIG. 7 and a coupon configured for tensile testing, according to one aspect of the disclosure;

FIG. 8B is a schematic cross-sectional view of the materials testing apparatus and the coupon configured for tensile testing shown in FIG. 8A, according to one aspect of the disclosure;

FIG. 9A is a schematic view of a materials testing apparatus of FIG. 7 and a coupon configured for compressive testing, according to one aspect of the disclosure;

FIG. 9B is a schematic cross-sectional view of the materials testing apparatus and the coupon configured for compressive testing shown in FIG. 9A, according to one aspect of the disclosure; and FIG. 10 is a block diagram of a method of testing a coupon having a toroidal portion, according to one aspect of the disclosure.

Figure 11:
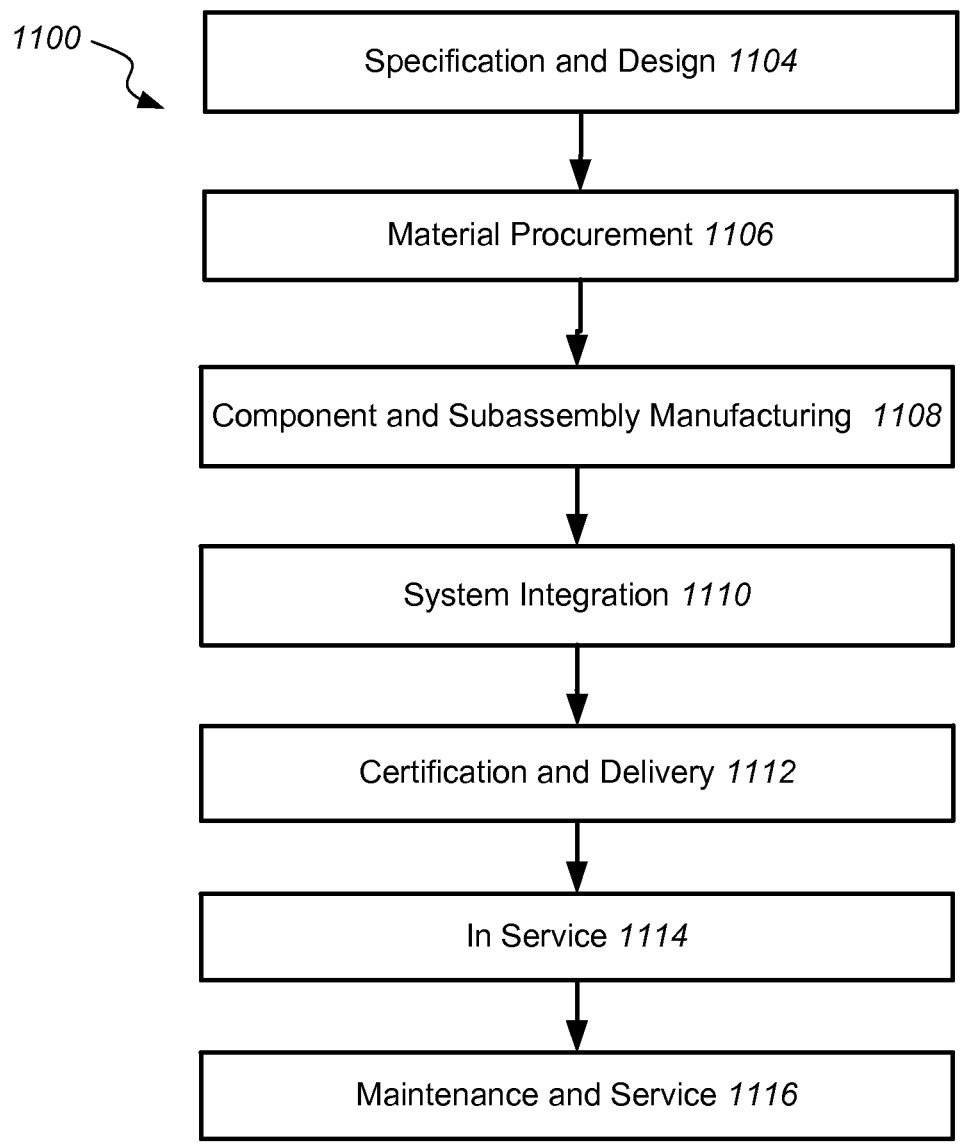
Figure 12:
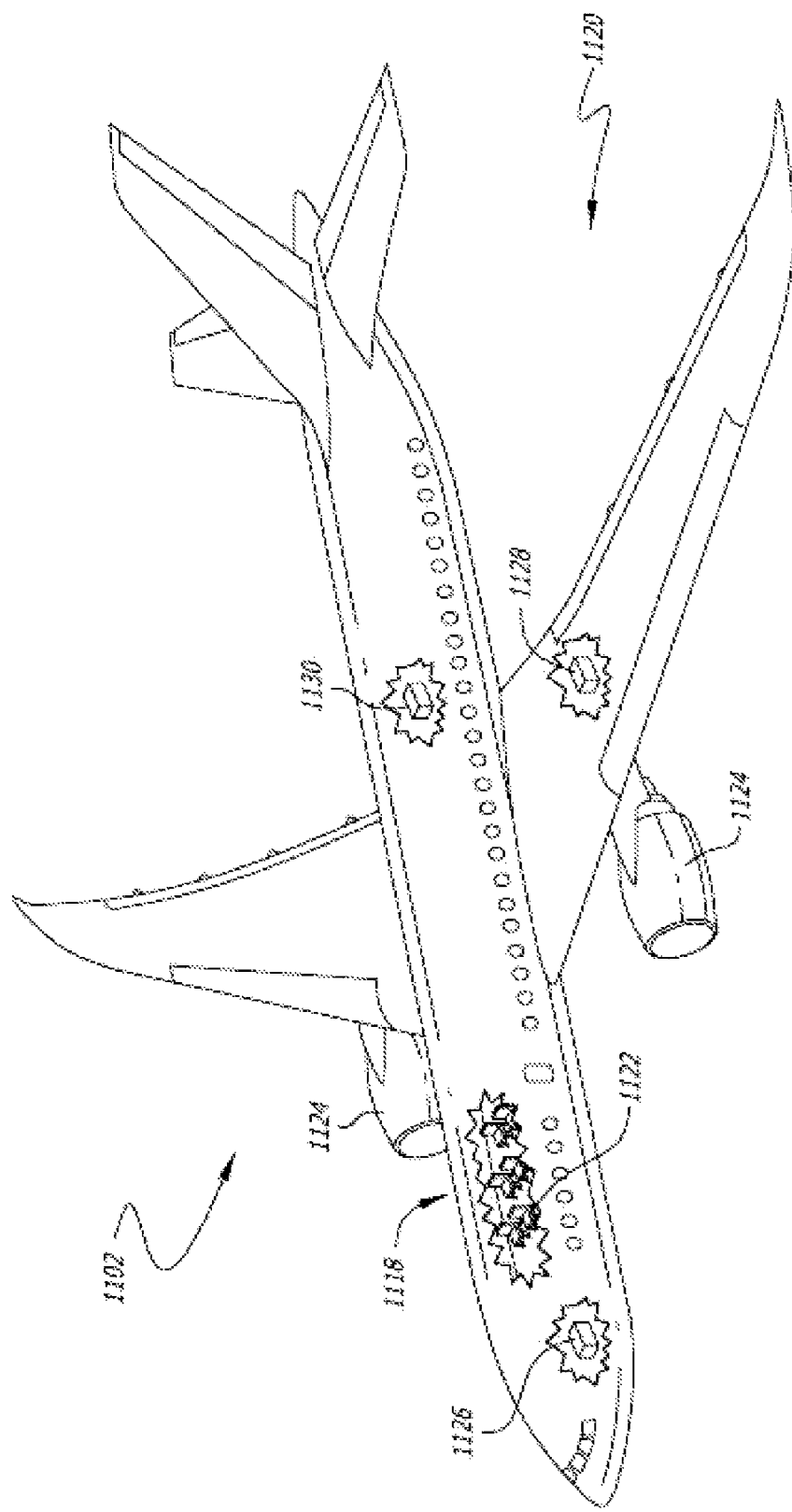

FIG. 11 is a block diagram of aircraft production and service methodology;

FIG. 12 is a schematic illustration of an aircraft.

In FIGS. 1, 4, and 7, referred to above, solid lines, if any, connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. It will be understood that not all relationships between the various disclosed elements are necessarily represented. Accordingly, couplings other than those depicted in the block diagrams may also exist. Dashed lines, if any, connecting the various elements and/or components represent couplings similar in function and purpose to those represented by solid lines; however, couplings represented by the dashed lines may either be selectively provided or may relate to alternative or optional aspects of the disclosure. Likewise, elements and/or components, if any, represented with dashed lines, indicate alternative or optional aspects of the disclosure. Environmental elements, if any, are represented with dotted lines. Virtual (imaginary) elements may also be shown for clarity. Those skilled in the art will appreciate that some of the features illustrated in each of FIGS. 1, 4, and 7 may be combined in various ways without the need to include other features described in these figures, other drawing figures, and/or the accompanying disclosure, even though such combination or combinations are not explicitly illustrated herein. Similarly, additional features not limited to the examples presented, may be combined with some or all of the features shown and described herein.

In FIGS. 6 and 10, referred to above, the blocks may also represent operations and/or portions thereof and lines connecting the various blocks do not imply any particular order or dependency of the operations or portions thereof. FIGS. 6 and 10 and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

DETAILED DESCRIPTION

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Referring generally to FIGS. 1-2D, and with particular reference to FIG. 1, one example of the present disclosure relates to a coupon 110. The coupon 110 includes a first surface 114 with a first circular channel 116 and a second surface 122 opposite and parallel to the first surface 114. The second surface 122 is spaced a distance D0 from the first surface 114 and includes a second circular channel 124 concentric with the first circular channel 116. The coupon 110 also includes a toroidal portion 132 between the first circular channel 116 and the second circular channel 124. The toroidal portion 132 includes a rectangular sectional portion 134.

Referring e.g. to FIGS. 1-2D, in one aspect of the disclosure, which may include at least a portion of the subject matter of any of the preceding and/or following examples and aspects, the the first circular channel 116 includes an outer radius R1$a$, an inner radius R1$b$, and a depth D1. The second circular channel 124 includes an outer radius R2$a$, an inner radius R2$b$, and a depth D2. The inner radius R2$b$ is greater than the outer radius R1$a$. A sum of the depth D1 and the depth D2 is greater than the distance D0.

With particular reference to FIG. 2B, the first circular channel 116 and the second circular channel 124 are concentrically located, but formed on opposite sides of the coupon 110. Because the inner radius R2$b$ is greater than the outer radius R1$a$, the Second Circular Channel 124 surrounds the first circular channel 116 such that there is material located between the two channels. Because the sum of depth D1 and D2 is greater than the distance D0, the material located between the first circular channel 116 and the second circular channel 124 forms the toroidal portion 132, which also includes the rectangular sectional portion 134.

As shown in FIGS. 1-2D, the coupon 110 includes the toroidal portion 132 that can be used in materials strength testing. The geometric configuration of the coupon 110 provides advantages over traditionally formed coupons that may include linear channels and ligaments. In particular, the coupon 110 is self-supporting, such that clamps or other fixtures are not needed during testing, as shown more fully with regard to FIGS. 8A-9B. Furthermore, the coupon 110 can be used in both tensile and compressive tests, as also shown more fully with regard to FIGS. 8A-9B. In addition, the circular channels 116 and 124 form the toroidal portion 132, which can resist torque or bending during strength testing. More particularly, when a stress is applied to the toroidal portion 132, the toroidal portion resists torqueing or bending due to its geometric configuration. In contrast, when stresses are applied to linear ligaments, which have been used in previous designs, the linear ligaments tend to torque or bend. This torqueing or bending of the linear ligaments often leads to premature failure of the coupon, thereby interfering with accurate strength measurements.

As shown in FIG. 2B, the first circular channel 116 and the second circular channel 124 can be curved or rounded at the base of the channel. In some examples, the base of a channel may be shaped as a semicircle. By curving or rounding the base of a channel, stress concentrations can be reduced during an application of stress to the toroidal portion 132.

Referring e.g. to FIGS. 1-2D, in one aspect of the disclosure, which may include at least a portion of the subject matter of any of the preceding and/or following examples and aspects, the coupon 110 is made of a composite material. Typically, composite materials include two or more materials that are combined within the structure of the composite material to yield desirable properties. For instance, composite materials may be lighter, stronger, and/or less expensive than a single material. One example includes fiber reinforced composites that are commonly used in spacecraft, aircraft, automobile frames, and other structures, because the material is lightweight but strong. Other examples include carbon composites, matrix composites, fiber reinforced polymers, etc. Although the present example includes the coupon 110 made of a composite material, it should be noted that various materials can be used to form the coupon 110 within the scope of this disclosure. Many different materials can be tested using the coupon 110 geometry and methods described herein. For instance, various materials can include metals, polymers, plastics, ceramics, etc.

Referring e.g. to FIGS. 1-2D, in one aspect of the disclosure, which may include at least a portion of the subject matter of any of the preceding and/or following examples and aspects, the composite material includes laminate layers. These laminate layers can be materials that are bonded together using heat, pressure, adhesives, or the like. Together, the laminate layers can provide improved properties, such as improved strength, stability, sound insulation, appearance, etc.

Referring e.g. to FIGS. 1-2D, in one aspect of the disclosure, which may include at least a portion of the subject matter of any of the preceding and/or following examples and aspects, the laminate layers are substantially parallel to the first surface 114 and the second surface 122. According to various examples, the laminate layers can be sheets of various materials bonded together by such techniques as heat, pressure, adhesives, or welding. The sheets can be positioned such that they are substantially parallel to the first surface 114 and the second surface 122 of the coupon 110.

Referring e.g. to FIGS. 1-2D, in one aspect of the disclosure, which may include at least a portion of the subject matter of any of the preceding and/or following examples and aspects, the composite material includes one of a polymer matrix, a ceramic matrix, or a metal matrix. Depending on the application, these materials can provide desirable properties. For instance, polymer matrix materials can include fiber-reinforced polymers, thermoplastic composites, shape memory polymers, etc. The shape memory polymers can be reheated and reshaped, and can be lightweight, rigid, and rapidly manufactured. Ceramic matrix composites can include hydroxyapatite reinforced with collagen fibers, ceramic and metal, and concrete. This type of material might be selected for fracture toughness instead of strength properties. Metal matrix composites can include metal fibers reinforcing other metals.

Referring e.g. to FIGS. 1-2D, in one aspect of the disclosure, which may include at least a portion of the subject matter of any of the preceding and/or following examples and aspects, the coupon 110 includes an indexing feature 130. The indexing feature 130 can be used as a reference location from which the first circular channel 116 and the second circular channel 124 can be positioned on the coupon 110. By positioning the first circular channel 116 and the second circular channel 124 from the same location, they can be more accurately positioned concentrically with respect to each other.

Referring e.g. to FIG. 1, in one aspect of the disclosure, which may include at least a portion of the subject matter of any of the preceding and/or following examples and aspects, the indexing feature 130 includes a void 131*a*. As described in more detail below, the void 131*a* can include an opening from which the first circular channel 116 and the second circular channel 124 can be positioned during manufacture of the coupon 110.

Referring e.g. to FIG. 2A, in one aspect of the disclosure, which may include at least a portion of the subject matter of any of the preceding and/or following examples and aspects, the void 131*a* includes a first opening 130*c* concentric with the first circular channel 116 and the second circular channel 124. The first opening 130*c* can extend through the coupon 110, such that it can be located from either side of the coupon 110. In some examples, hole saws can be used to form the first circular channel 116 and the second circular channel 124. Each of the hole saws can include a centering bit that can be used to position the respective hole saw relative to the coupon 110. Specifically, a centering bit can engage with the first opening 130*c* and an associated hole saw can form the first circular channel 116. Another hole saw can be used to form the second circular channel 124, with an associated centering bit engaging the first opening 130*c* from the opposite side of the coupon 110. By using the centering bits, the first circular channel 116 and the second circular channel 124 can be positioned concentrically.

Referring e.g. to FIG. 2A, in one aspect of the disclosure, which may include at least a portion of the subject matter of any of the preceding and/or following examples and aspects, the void 131*a* includes a second opening 130*a* that is non-concentric with the first circular channel 116 and the second circular channel 124. The second opening 130*a* can provide a reference point from which the positions of the first circular channel 116 and the second circular channel 124 can be determined. In one example, these positions can be manually determined, such as by a mechanical clamp and positioning arm(s) or by manual measurements. In another example, these positions can be determined by a computerized machining apparatus, such as a CNC milling machine, or other computing device or controller. In FIG. 2A, both openings 130*c* and 130*a* have been illustrated for ease of reference only. Those skilled in the art will appreciate that the first opening 130*c* and the second opening 130*a* need not be both formed in the same coupon. Either opening alone may be used to identify locations of the first circular channel 116 and the second circular channel 124.

Referring e.g. to FIGS. 2A-2B, in one aspect of the disclosure, which may include at least a portion of the subject matter of any of the preceding and/or following examples and aspects, the second opening 130*a* is located outside of the outer radius R2*a* of the second circular channel 124. By locating the second opening 130*a* outside of and away from the second circular channel 124, the second opening 130a avoids interfering with the toroidal portion 132 (see FIG. 2B) during strength testing of the coupon. In addition, as shown in FIGS. 3A-3C, a single second opening 130a can be used to position multiple coupons on a single material blank. Specifically, each of the circular channels shown in FIGS. 3A-3C can be positioned relative to the second opening 130a. In some examples, such as the one shown, the coupons can include different features such as circular channels having differing depths D2e and D2f. Specifically, the two leftmost coupons have circular channels with depths of D2e, and the two rightmost coupons have circular channels with depths of D2f. However, various configurations of coupons can be included on a single material blank, depending on the application.

Referring e.g. to FIG. 1, in one aspect of the disclosure, which may include at least a portion of the subject matter of any of the preceding and/or following examples and aspects, one portion of the void 131a is in the first surface 114 and another portion of the void 131a is in the second surface 122. As described above, the void 131a can include an opening from which the first circular channel 116 and the second circular channel 124 can be positioned during manufacture of the coupon 110. Accordingly, the void 131a can extend to both the first surface 114 and the second surface 122, thereby allowing the first circular channel 116 and the second circular channel 124 to be positioned relative to the same reference location.

Referring e.g. to FIGS. 1-2A, in one aspect of the disclosure, which may include at least a portion of the subject matter of any of the preceding and/or following examples and aspects, the indexing feature 130 includes a protuberance 131b. This protuberance can include a feature of the coupon, such as a corner, edge, etc.

Referring e.g. to FIGS. 1-2A, in one aspect of the disclosure, which may include at least a portion of the subject matter of any of the preceding and/or following examples and aspects, the protuberance 131b is a corner 130b of the coupon 110. By using the corner 130b of the coupon 110 as a reference location, no additional openings or features need to be machined into the coupon 110. The corner 130b can be used to manually position the first circular channel 116 and the second circular channel 124 in some examples. In other examples, the corner 130b can be used by a computerized milling machine or other computer or controller to position the first circular channel 116 and the second circular channel 124.

Referring generally to FIGS. 4-5C, and with particular reference to FIG. 4, one example of the present disclosure relates to a machining apparatus 100. The machining apparatus 100 includes a first hole saw 102 having a first longitudinal symmetry axis 180, a first shank 126, and a first cylindrical saw blade 128 coupled to the first shank 126. The first cylindrical saw blade 128 includes a first diameter 196, a length L3 along the first longitudinal symmetry axis 180, and at least one first slot 104 including a length L4 parallel to the first longitudinal symmetry axis 180. The length L4 is less than the length L3.

According to various examples, the first hole saw 102 can be used to form a circular channel in a material blank 112. In particular, with reference to FIG. 1, the first hole saw 102 can be used to form the first circular channel 116, having the outer radius R1a and the inner radius R1b in the first surface 114. The first hole saw 102 can be operated manually or as part of a computerized machining system or other computer or controller 108.

Referring e.g. to FIGS. 4-5C, in one aspect of the disclosure, which may include at least a portion of the subject matter of any of the preceding and/or following examples and aspects, the at least one first slot 104 includes a width W1 along a direction perpendicular to the first longitudinal symmetry axis 180. The length L4 is greater than the width W1. The at least one first slot 104 allows fluids and debris to pass through when the first hole saw 102 is operating. With reference to FIG. 5C, shown is a cross-sectional view of the first cylindrical saw blade 128 cutting a circular channel 120. In the present example, the first cylindrical saw blade 128 includes two slots 104, through which fluids and debris can pass 506 between the inside and outside of the first cylindrical saw blade 128. As the first cylindrical saw blade 128 cuts through a material to form the circular channel 120, coolant fluids can be used to lubricate and cool the tool and material being cut, and debris from the cut material is produced. Allowing the fluids and debris to flow in and out of the first cylindrical saw blade 128 through slot(s) 104 provides a more efficient and smooth cutting process.

The length L4 of the first slot(s) 104 can be adjusted depending on the application. In various examples, the length L4 can be less than the depth of the cut to be produced, and still provide adequate flow of fluids and debris to provide improvements over traditional saw blades. The width W1 is typically less than length L4, partially because limiting the width W1 allows more cutting surface to exist on the cylindrical saw blade 128.

Referring e.g. to FIGS. 4-5C, in one aspect of the disclosure, which may include at least a portion of the subject matter of any of the preceding and/or following examples and aspects, the first cylindrical saw blade 128 includes a first blade tip 118 having an abrasive coating. The abrasive coating can aid in cutting through various materials. The abrasive coating can provide additional friction and can include materials suited to cut through a particular material. For instance, tungsten carbide, diamond, or other materials can be used as the abrasive coating. In some examples, other coatings can be used such as titanium composites, etc. to improve strength. In addition, the abrasive coating can include burs which can include geometries and shapes that allow easier cutting. The burs can also have additional coatings that add to strength and other desirable properties.

Referring e.g. to FIGS. 4-5C, in one aspect of the disclosure, which may include at least a portion of the subject matter of any of the preceding and/or following examples and aspects, the abrasive coating is a diamond coating. A diamond coating can be used as the abrasive coating to provide a strong cutting surface that also has a long life. The diamond coating can be used to cut through a variety of materials.

Referring e.g. to FIG. 4, in one aspect of the disclosure, which may include at least a portion of the subject matter of any of the preceding and/or following examples and aspects, the first hole saw 102 includes a first centering bit 182 located along the first longitudinal symmetry axis 180 that is at least partially surrounded by the first cylindrical saw blade 128. In various examples, the first centering bit 182 can be attached to the first shank 126 and located within an enclosed area of the first cylindrical saw blade 128. The first centering bit 182 can be used to position the first hole saw 102 with respect to the material to be drilled. In particular, the first centering bit 182 can engage a pilot hole that serves as the indexing feature 130. In particular, the pilot hole can serve as the first opening 130c, as described more fully above with regard to FIGS. 1-2A. Engaging with the pilot hole can both position and stabilize the first hole saw 102 during drilling.

Referring e.g. to FIGS. 4-5C, in one aspect of the disclosure, which may include at least a portion of the subject matter of any of the preceding and/or following examples and aspects, the machining apparatus 100 includes a second hole saw 184. The second hole saw 184 has a second longitudinal symmetry axis 188, a second shank 186, and a second cylindrical saw blade 192 coupled to the second shank 186. The second cylindrical saw blade 192 includes a second diameter 198 greater than the first diameter 196, a length L5 along the second longitudinal symmetry axis 188, and at least one second slot 197 including a length L6 parallel to the second longitudinal symmetry axis 188. The length L6 is less than the length L5.

According to various examples, the second hole saw 184 can be used to form a circular channel in the material blank 112. In particular, with reference to FIG. 1, the second hole saw 184 can be used to form the second circular channel 124, having the outer radius R2a and inner radius R2b in the second surface 122. The second hole saw 184 can be operated manually or as part of a computerized machining system or other computer or controller 108.

Referring e.g. to FIGS. 4-5C, in one aspect of the disclosure, which may include at least a portion of the subject matter of any of the preceding and/or following examples and aspects, the at least one second slot 197 includes a width W2 along a direction perpendicular to the second longitudinal symmetry axis 188. The length L6 is greater than the width W2.

The at least one second slot 197 allows fluids and debris to pass through when the second hole saw 184 is operating. Although the second hole saw 184 is not explicitly shown in FIGS. 5A-5C, the at least one second slot 197 operates similarly to the at least one first slot 104 shown in these figures. In particular, as the second cylindrical saw blade 192 cuts through a material to form a cylindrical channel, coolant fluids can be used to lubricate and cool the tool and material being cut, and debris from the cut material is produced. Allowing the fluids and debris to flow in and out of the second cylindrical saw blade 192 through slot(s) 197 provides a more efficient and smooth cutting process.

The length L6 of the second slot(s) 197 can be adjusted depending on the application. In various examples, the length L6 can be less than the depth of the cut to be produced, and still provide adequate flow of fluids and debris to provide improvements over traditional saw blades. The width W2 is typically less than length L6, partially because limiting the width W2 allows more cutting surface to exist on the cylindrical saw blade 192.

Referring e.g. to FIG. 4, in one aspect of the disclosure, which may include at least a portion of the subject matter of any of the preceding and/or following examples and aspects, the second cylindrical saw blade 192 includes a second blade tip 194 having an abrasive coating. The An abrasive coating can aid in cutting through various materials. The abrasive coating can provide additional friction and can include materials suited to cut through a particular material. For instance, tungsten carbide, diamond, or other materials can be used as the abrasive coating. In some examples, other coatings can be used such as titanium composites, etc. to improve strength. In addition, the abrasive coating can include burs which can include geometries and shapes that allow easier cutting. The burs can also have additional coatings that add to strength and other desirable properties.

Referring e.g. to FIG. 4, in one aspect of the disclosure, which may include at least a portion of the subject matter of any of the preceding and/or following examples and aspects, the abrasive coating is a diamond coating. A diamond coating can be used as an abrasive coating to provide a strong cutting surface that also has a long life. The diamond coating can be used to cut through a variety of materials.

Referring e.g. to FIG. 4, in one aspect of the disclosure, which may include at least a portion of the subject matter of any of the preceding and/or following examples and aspects, the second hole saw 184 includes a second centering bit 190 along the second longitudinal symmetry axis 188. The second centering bit 190 is at least partially surrounded by the second cylindrical saw blade 192. In various examples, the second centering bit 190 can be attached to the second shank 186 and located within an enclosed area of the second cylindrical saw blade 192. The second centering bit 190 can be used to position the second hole saw 184 with respect to the material to be drilled. In particular, the second centering bit 190 can engage a pilot hole that serves as the indexing feature 130. In particular, the pilot hole can serve as the first opening 130c, as described more fully above with regard to FIGS. 1-2A. Engaging with the pilot hole can both position and stabilize the second hole saw 184 during drilling.

Referring generally to FIGS. 1-6, and with particular reference to FIG. 6, one example of the present disclosure relates to a method of making the coupon 110 from the material blank 112, as indicated at 600. As shown in FIG. 1, the material blank 112 includes the first surface 114 on a first side of the material blank 112 and the second surface 122 opposite and parallel to the first surface 114 on a second side of the material blank 112. The second surface 122 is spaced the distance D0 from the first surface 114.

With particular reference to FIG. 6, the method of making a coupon from the material blank 112 includes forming the first circular channel 116 in the material blank 112 from the first side, such that the first circular channel 116 is perpendicular to the first surface 114 and includes the inner radius R1b, the outer radius R1a, and the depth D1, as indicated at 604. The depth D1 is less than the distance D0. As indicated at 608, the method of making the coupon 110 from the material blank 112 also includes forming the second circular channel 124 in the material blank 112 from the second side, such that the second circular channel 124 is perpendicular to the second surface 122 and concentric with the first circular channel 116. The second circular channel 124 includes the depth D2, the inner radius R2b, and the outer radius R2a. The depth D2 is less than the distance D0. A sum of the depth D1 and the depth D2 is greater than the distance D0. The inner radius R2b is greater than the outer radius R1a.

By forming the first circular channel 116 and the second circular channel 124 as described in this method, the coupon 110 having various features described with regard to FIGS. 1-2D is produced. In particular, the coupon 110 is formed to include the toroidal portion 132 between the first circular channel 116 and the second circular channel 124. Although the method described in the present example includes forming the first circular channel at 604 before forming the second circular channel at 608, the second circular channel can be formed before the first circular channel in some examples, without deviating from the scope of this disclosure.

The method of making a coupon as described requires fewer steps than traditional methods yielding coupons with linear ligaments. Although typical coupons having linear ligaments require four machining operations to provide two linear ligaments, the method described herein requires only two machining operations to produce the toroidal portion 132, according to various examples. This reduction in machining operations can both generate cost savings and improve accuracy of the machined pieces.

Referring e.g. to FIG. 6, in one aspect of the disclosure, which may include at least a portion of the subject matter of any of the preceding and/or following examples and aspects, forming the first circular channel 116 includes identifying a first location of the first circular channel 116 using the indexing feature 130, as indicated at 602, and forming the second circular channel 124 includes identifying a second location of the second circular channel 124 using the indexing feature 130, as indicated at 606. In particular, the indexing feature 130 is located on the first surface 114 and the first circular channel 116 is positioned relative to the indexing feature 130 at 602. This position can be determined manually or by using a controller 108 (see FIG. 4) such as a computer or computerized machining apparatus. At 604, the first circular channel 116 is formed at this location. Next, at 606, the indexing feature 130 is located on the second surface 122 and the second circular channel 124 is positioned relative to the indexing feature 130 at 606. This position can be determined manually or by using the controller 108 (see FIG. 4) such as a computer or computerized machining apparatus. At 608, the second circular channel 124 is formed at this location.

Referring e.g. to FIGS. 1-6, in one aspect of the disclosure, which may include at least a portion of the subject matter of any of the preceding and/or following examples and aspects, the indexing feature 130 is the first opening 130c concentric with the first circular channel 116 and the second circular channel 124. The first opening 130c can extend through the coupon 110, such that it can be located from either side of the coupon 110. By positioning both the first circular channel 116 and the second circular channel 124 from the same location, they can be more accurately positioned concentrically with respect to each other.

Referring e.g. to FIGS. 1-6, in one aspect of the disclosure, which may include at least a portion of the subject matter of any of the preceding and/or following examples and aspects, the first opening 130c is a pilot hole. Identifying the first location of the first circular channel 116 includes aligning the first centering bit 182 of the first hole saw 102 with the pilot hole. Moreover, forming the first circular channel 116 includes drilling the material blank 112 with the first hole saw 102 at the first location. In particular, the first centering bit 182 engages with the pilot hole from the first surface 114 and the first hole saw forms the first circular channel 116.

Referring e.g. to FIGS. 1-6, in one aspect of the disclosure, which may include at least a portion of the subject matter of any of the preceding and/or following examples and aspects, identifying the second location of the second circular channel 124 includes aligning the second centering bit 190 of the second hole saw 184 with the pilot hole. In addition, forming the second circular channel 124 includes drilling the material blank 112 with the second hole saw 184 at the second location. In particular, the second centering bit 190 engages with the pilot hole from the second surface 122 and the second hole saw 184 forms the second circular channel 124. By engaging the first and second centering bits with the same pilot hole, the first circular channel 116 and the second circular channel 124 can be positioned concentrically.

Referring e.g. to FIGS. 1-6, in one aspect of the disclosure, which may include at least a portion of the subject matter of any of the preceding and/or following examples and aspects, the indexing feature 130 is the second opening 130a non-concentric with the first circular channel 116 and the second circular channel 124. The indexing feature 130 is located outside of the outer radius R2a of the second circular channel 124. By locating the second opening 130a outside of and away from the second circular channel 124, the second opening 130a avoids interfering with the toroidal portion 132 (see FIG. 2B) during strength testing of the coupon. In addition, as shown in FIGS. 3A-3C, a single second opening 130a can be used to position multiple coupons on a single material blank. Specifically, each of the circular channels shown in FIGS. 3A-3C can be positioned relative to the second opening 130a.

Referring e.g. to FIGS. 1-6, in one aspect of the disclosure, which may include at least a portion of the subject matter of any of the preceding and/or following examples and aspects, the indexing feature 130 is the corner 130b of the coupon 110. By using the corner 130b of the coupon 110 as a reference location, no additional openings or features need to be machined into the coupon 110. The corner 130b can be used to manually position the first circular channel 116 and the second circular channel 124 in some examples. In other examples, the corner 130b can be used by a computerized milling machine or other computer or controller to position the first circular channel 116 and the second circular channel 124.

Referring e.g. to FIG. 6, in one aspect of the disclosure, which may include at least a portion of the subject matter of any of the preceding and/or following examples and aspects, identifying the first location of the first circular channel 116 includes sensing a position of the indexing feature 130, as indicated at 601. For instance, the controller 108 (see FIG. 4) such as a computer, computerized machining apparatus, or the like, can be used to sense the position of the indexing feature 130.

Referring e.g. to FIGS. 1-6, in one aspect of the disclosure, which may include at least a portion of the subject matter of any of the preceding and/or following examples and aspects, the first location of the first circular channel 116 is identified based on the position of the indexing feature 130. In particular, the indexing feature 130 is located on the first surface 114 at 602 and the first circular channel 116 is positioned relative to the indexing feature 130. This position can be determined manually or by using the controller 108 (see FIG. 4) such as a computer, computerized machining apparatus, or the like.

Referring e.g. to FIGS. 1-6, in one aspect of the disclosure, which may include at least a portion of the subject matter of any of the preceding and/or following examples and aspects, the second location of the second circular channel 124 is identified based on the position of the indexing feature 130. In particular, the indexing feature 130 is located on the second surface 122 at 606 and the second circular channel 124 is positioned relative to this indexing feature 130. This position can be determined manually or by using the controller 108 (see FIG. 4) such as a computer or computerized machining apparatus. At 608, the second circular channel 124 is formed at this location.

Referring e.g. to FIGS. 1-6, in one aspect of the disclosure, which may include at least a portion of the subject matter of any of the preceding and/or following examples and aspects, forming the first circular channel 116 and the second circular channel 124 includes computer-numerical-control (CNC) machining the material blank 112. Specifically, a CNC machine, or the like, can be used to position and drill the first circular channel 116 and the second circular channel 124. The CNC machine can automatically perform the machining operations on the coupon 110 based on user inputs, etc.

Referring e.g. to FIGS. 1-6, in one aspect of the disclosure, which may include at least a portion of the subject matter of any of the preceding and/or following examples and aspects, forming the first circular channel 116 and the second circular channel 124 includes locating the indexing feature 130 and identifying the first location of the first circular channel 116 and the second location of the second circular channel 124 based on a position of the indexing feature 130. In particular, the indexing feature 130 is located on the first surface 114 at 602 and the first circular channel 116 is positioned relative to the indexing feature 130. This position can be determined manually or by using the controller 108 (see FIG. 4) such as a computer or computerized machining apparatus. At 604, the first circular channel 116 is formed at this location. Next, the indexing feature 130 is located on the second surface 122 at 606 and the second circular channel 124 is positioned relative to this indexing feature 130. This position can be determined manually or by using the controller 108 (see FIG. 4) such as a computer or computerized machining apparatus. At 608, the second circular channel 124 is formed at this location.

Referring generally to FIGS. 7-10, and with particular reference to FIGS. 1 and 10, one example of the present disclosure relates to a method of testing the coupon 110. The coupon 110 includes the first surface 114 including the first circular channel 116 and the second surface 122 opposite and parallel to the first surface 114. The second surface 122 is spaced the distance D0 from the first surface 114 and includes the second circular channel 124 that is concentric with the first circular channel 116. The toroidal portion 132 is located between the first circular channel 116 and the second circular channel 124. The toroidal portion 132 includes the rectangular sectional portion 134. The first surface 114 includes a first inner region 160 located within the inner radius R1$b$ of the first circular channel 116 and a first outer region located outside the outer radius R1$a$ of the first circular channel 116. The second surface 122 includes a second inner region 164 located within the inner radius R2$b$ of the second circular channel 124 and a second outer region 166 located outside the outer radius R2$a$ of the second circular channel 124. The outer radius R1$a$ is less than the inner radius R2$b$.

With particular reference to FIG. 10, the method of testing the coupon 110, as indicated at 1000, includes exerting a stress on the toroidal portion 132 of the coupon 110 at 1006 and measuring deformation of the toroidal portion 132 responsive to the stress at 1008. This deformation can be measured by the extensometer 152 (FIG. 7), or the like, in various examples. A unique feature of the coupon 110, as described with regard to FIGS. 1-2D, is that it can be used for either tensile or compressive testing. Accordingly, identical coupons 110 can be used to test tensile and compressive strengths of the same material. Because the identical coupons 110 can be used for both tests, producing coupons 110 for strength testing is more efficient and cost effective.

Referring e.g. to FIGS. 8A-8B and FIG. 10, in one aspect of the disclosure, which may include at least a portion of the subject matter of any of the preceding and/or following examples and aspects, the stress is a tensile stress. In FIG. 10, a determination can be made that the tensile stress is to be applied at 1001. Applying the tensile stress to the coupon 110 and measuring the corresponding strain of the toroidal portion 132 and/or the rectangular sectional portion 134 allows a tensile strength of the material within the coupon 110 to be determined. The tensile strength is also commonly referred to as ultimate tensile strength and ultimate strength. With reference to FIG. 7, strain can be measured with the extensometer 152, or the like.

Referring e.g. to FIGS. 8A-8B, and FIG. 10, in one aspect of the disclosure, which may include at least a portion of the subject matter of any of the preceding and/or following examples and aspects, exerting the tensile stress on the toroidal portion 132 of the coupon 110 includes simultaneously applying a first force F1 to the first inner region 160 in a direction perpendicular to the first surface 114 and the second surface 122, a second force F2 to the second outer region 166, and no force to the first outer region 162 and second inner region 164, as indicated at 1007. The first force F1 and the second force F2 face each other and are equal in magnitude. As shown in FIG. 8B, first force F1 and second force F2 are applied to the coupon 110 without the need for bonding blocks or adhesives. This provides a significant advantage over traditional tensile testing systems, which require an extra step of bonding the blocks to the coupon. This configuration and method of testing results in reduced materials and time costs. In addition, because the coupon 110 is self-supporting, due to the geometry of the toroidal portion 132, no additional fixtures or supports are needed to prepare or secure the coupon 110 for testing.

Referring e.g. to FIGS. 8A-8B, in one aspect of the disclosure, which may include at least a portion of the subject matter of any of the preceding and/or following examples and aspects, the first force F1 is applied by a first punch 144$a$. As shown in FIG. 8A, the first punch 144$a$ can have a circular cross section in some examples. However, the first punch 144$a$ can also include other cross-sectional shapes such as a pentagon, hexagon, octagon, etc., without deviating from the scope of this disclosure. In addition, the force F1 can be applied through first punch 144$a$ by a materials test frame 150 (FIG. 7), also referred to as a universal testing machine, according to various examples.

Referring e.g. to FIGS. 8A-8B and FIG. 10, in one aspect of the disclosure, which may include at least a portion of the subject matter of any of the preceding and/or following examples and aspects, the first punch 144$a$ is substantially concentrically aligned with the first circular channel 116 and the second circular channel 124 when the first force F1 is applied by the first punch 144$a$ to the first inner region 160, as indicated at 1002. By concentrically aligning the first punch 144$a$ with the first circular channel 116 and the second circular channel 124, the first force F1 can be applied more evenly to the rectangular sectional portion 134. This alignment can result in more evenly distributed strain of the rectangular sectional portion 134, thereby resulting in a more accurate determination of the tensile strength of the material tested.

Referring e.g. to FIGS. 8A-8B, in one aspect of the disclosure, which may include at least a portion of the subject matter of any of the preceding and/or following examples and aspects, the first punch 144$a$ contacts the first inner region 160 without contacting the first outer region 162 when the first force F1 is applied by the first punch 144$a$ to the first inner region 160. As shown in FIG. 8B, applying a first force F1 to the first inner region 160 without applying any force to first outer region 162 allows the rectangular sectional portion 134 to be in tension. If first force F1 were also applied to first outer region 162, the rectangular sectional portion 134 would not be subject to the same tension, and the forces throughout the coupon would be distributed differently.

Referring e.g. to FIGS. 8A-8B, in one aspect of the disclosure, which may include at least a portion of the preceding and/or following examples and aspects, the first punch 144$a$ includes a first circular circumference P1. As described above, the first punch 144a can have a circular cross section according to various examples. By having a circular cross section, the first punch 144a can apply the first force F1 to the first inner region 160 without contacting the first outer region 162. In other examples, the first punch 144a can have other cross-sectional shapes that allow the first punch 144a to contact the first inner region 160 without contacting the first outer region 162. For instance, a pentagon, hexagon, octagon, etc. can be used.

Referring e.g. to FIGS. 8A-8B, in one aspect of the disclosure, which may include at least a portion of the subject matter of any of the preceding and/or following examples and aspects, the second force F2 is applied by a first plate 138a having a first circular opening C1. As shown, the first plate 138a is supported by a base plate 176. In some examples, this base plate 176 can be part of a materials test frame 150 (FIG. 7) or can be assembled with the first plate 138a within the materials test frame 150. In some examples, the second force F2 can be applied by a support structure within the materials test frame 150, such as by a stationary support. In the present example, by having a first circular opening C1, the second force F2 can be applied to the second outer region 166 while the first force F1 is applied to the first inner region 160. In this configuration, the rectangular sectional portion 134 is subjected to tensile stresses when the first force F1 and second force F2 are applied. It should be recognized that other shaped openings can be used in first plate 138a in some examples. For instance, a pentagonal, hexagonal, octagonal, or other shaped opening can be used to support the second outer region 166.

Referring e.g. to FIGS. 8A-8B and FIG. 10, in one aspect of the disclosure, which may include at least a portion of the subject matter of any of the preceding and/or following examples and aspects, the first circular opening C1 is substantially concentrically aligned with the first circular channel 116 and the second circular channel 124 when the second force F2 is applied by the first plate 138a to the second outer region 166, as indicated at 1003. By aligning the first circular opening C1 with the first circular channel 116 and the second circular channel 124, the coupon 110 can be more evenly supported by the first plate 138a. Furthermore, the second outer region 166 can be supported by the first plate 138a while the second inner region 164 can remain unsupported when the first circular opening C1 is aligned with the first circular channel 116 and the second circular channel 124.

Referring e.g. to FIGS. 8A-8B, in one aspect of the disclosure, which may include at least a portion of the subject matter of any of the preceding and/or following examples and aspects, the first plate 138a contacts the second outer region 166 without contacting the second inner region 164. By having the first plate 138a contact the second outer region 166 without contacting the second inner region 164, the second force F2 can be applied to the second outer region 166. In this configuration, the rectangular sectional portion 134 is subjected to tensile stresses when the first force F1 and second force F2 are applied.

Referring e.g. to FIGS. 9A-9B and FIG. 10, in one aspect of the disclosure, which may include at least a portion of the subject matter of any of the preceding and/or following examples and aspects, the stress is a compressive stress. In FIG. 10, a determination can be made that the compressive stress is to be applied at 1001. Compressive stress is used to determine the compressive strength of a material, which is the ability of the material to withstand loads that tend to reduce the material's size. This compressive strength is computed by plotting force versus deformation of the material.

Referring e.g. to FIGS. 9A-9B and FIG. 10, in one aspect of the disclosure, which may include at least a portion of the subject matter of any of the preceding and/or following examples and aspects, exerting the compressive stress on the toroidal portion 132 of the coupon 110 includes simultaneously applying a third force F3 to the second inner region 164 in a direction perpendicular to the first surface 114 and the second surface 122, a fourth force F4 to the first outer region 162, and no force to the first inner region 160 and the second outer region 166, as indicated at 1014. The third force F3 and the fourth force F4 face each other and are equal in magnitude. In this configuration, the rectangular sectional portion 134 is subjected to a compressive stress when the third force F3 and fourth force F4 are applied.

Referring e.g. to FIGS. 9A-9B, in one aspect of the disclosure, which may include at least a portion of the subject matter of any of the preceding and/or following examples and aspects, third force F3 is applied by a second punch 144b. In an alternative example, the second punch 144b can be a hollow cylinder that allows the third force F3 to be aligned with the toroidal portion 132 of the coupon.

Referring e.g. to FIGS. 9A-9B and FIG. 10, in one aspect of the disclosure, which may include at least a portion of the subject matter of any of the preceding and/or following examples and aspects, the second punch 144b is substantially concentrically aligned with the first circular channel 116 and the second circular channel 124 when the third force F3 is applied by the second punch 144b to the second inner region 164, as indicated at 1010. By concentrically aligning the second punch 144b with the first circular channel 116 and second circular channel 124, the third force F3 can be applied more evenly to the rectangular sectional portion 134. This alignment can result in more evenly distributed strain of the rectangular sectional portion 134, thereby resulting in a more accurate determination of the compressive strength of the material tested.

Referring e.g. to FIGS. 9A-9B, in one aspect of the disclosure, which may include at least a portion of the subject matter of any of the preceding and/or following examples and aspects, the second punch 144b contacts the second inner region 164 without contacting the second outer region 166 when the third force F3 is applied by the second punch 144b to the second inner region 164. By applying third force F3 and fourth force F4 to opposite sides of the rectangular sectional portion 134 of the coupon 110, as shown in FIG. 9B, the compressive stress is applied to the rectangular sectional portion 134.

Referring e.g. to FIGS. 9A-9B, in one aspect of the disclosure, which may include at least a portion of the subject matter of any of the preceding and/or following examples and aspects, the second punch 144b includes a second circular circumference. In the present example, the second punch 144b has a circular cross section, as shown in FIG. 9A. However, the second punch 144 can include other cross-sectional shapes in other examples. For instance, the second punch can have a square, pentagon, hexagon, octagon, or any other shape, as its cross section.

Referring e.g. to FIGS. 9A-9B, in one aspect of the disclosure, which may include at least a portion of the subject matter of any of the preceding and/or following examples and aspects, the fourth force F4 is applied by a second plate 138b having a second circular opening C2. As shown, the second plate 138b is supported by the base plate 176. In some examples, this base plate 176 can be part of materials test frame 150 or can be assembled with the second plate 138b within the materials test frame 150 (FIG. 7). In some examples, the fourth force F4 can be applied by a support structure within the materials test frame 150, such as by a stationary support. In the present example, by having the second circular opening C2, the fourth force F4 can be applied to the first outer region 162 while the third force F3 is applied to the second inner region 166. In this configuration, the rectangular sectional portion 134 is subjected to compressive stresses when the third force F3 and second force F4 are applied. It should be recognized that other shaped openings can be used in second plate 138b in some examples. For instance, a pentagonal, hexagonal, octagonal, or other shaped opening can be used to support the first outer region 162.

Referring e.g. to FIGS. 9A-9B and FIG. 10, in one aspect of the disclosure, which may include at least a portion of the subject matter of any of the preceding and/or following examples and aspects, the second circular opening C2 is substantially concentrically aligned with the first circular channel 116 and the second circular channel 124 when the fourth force F4 is applied by the second plate 138b to the first outer region 162, as indicated at 1012. By aligning the second circular opening C2 with the first circular channel 116 and the second circular channel 124, the coupon 110 can be more evenly supported by the second plate 138b.

Referring e.g. to FIGS. 9A-9B, in one aspect of the disclosure, which may include at least a portion of the subject matter of any of the preceding and/or following examples and aspects, the second plate 138b contacts the first outer region 162 without contacting the first inner region 160. In this configuration, the compressive stress is applied to the rectangular sectional portion 134 when third force F3 and fourth force F4 are applied.

Referring e.g. to FIG. 10, in one aspect of the disclosure, which may include at least a portion of the subject matter of any of the preceding and/or following examples and aspects, the method of testing the coupon 110 includes exposing the toroidal portion 132 to environmental conditions at 1004. Traditionally, tensile tests required adhering bonding blocks to a coupon and pulling the bonding blocks to apply a tensile stress to the coupon. Adhering the bonding blocks to a coupon requires an additional step in the testing process, and the adhesives required to bond the blocks to a coupon can fail when the coupon is exposed to environmental conditions, such as moisture and elevated temperatures. One advantage of the method described in the present disclosure is that no bonding blocks or adhesives are needed to prepare the coupon 110 for testing, thereby saving both time and cost for each coupon 110 tested. Instead, the materials testing apparatus 136, as described in conjunction with FIG. 7, is insensitive to environmental conditions. Accordingly, the coupon 110 can be exposed to environmental conditions within the materials testing apparatus 136 without concern about premature failure.

Referring e.g. to FIG. 10, in one aspect of the disclosure, which may include at least a portion of the subject matter of any of the preceding and/or following examples and aspects, the environmental conditions 1004 include moisture. Because the materials testing apparatus 136 is insensitive to moisture, the toroidal portion 132 of the coupon 110 can be exposed to moisture, without concern that the materials testing apparatus 136 or any fixtures surrounding the coupon will fail prematurely under such conditions.

Referring e.g. to FIG. 10, in one aspect of the disclosure, which may include at least a portion of the subject matter of any of the preceding and/or following examples and aspects, the environmental conditions 1004 include a controlled temperature. Because the materials testing apparatus 136 is insensitive to temperature variations, the toroidal portion 132 of the coupon 110 can be exposed to various temperatures, without risk that the materials testing apparatus 136 or any fixtures surrounding the coupon will fail under such conditions.

Examples of the disclosure may be described in the context of an aircraft manufacturing and service method 1100 as shown in FIG. 11 and an aircraft 1102 as shown in FIG. 12. During pre-production, illustrative method 1100 may include specification and design 1104 of the aircraft 1102 and material procurement 1106. During production, component and subassembly manufacturing 1108 and system integration 1110 of the aircraft 1102 take place. Thereafter, the aircraft 1102 may go through certification and delivery 1112 to be placed in service 1114. While in service by a customer, the aircraft 1102 is scheduled for routine maintenance and service 1116 (which may also include modification, reconfiguration, refurbishment, and so on).

Each of the processes of the illustrative method 1100 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 11, the aircraft 1102 produced by the illustrative method 1100 may include an airframe 1118 with a plurality of high-level systems 1120 and an interior 1122. Examples of high-level systems 1120 include one or more of a propulsion system 1124, an electrical system 1126, a hydraulic system 1128, and an environmental system 1130. Any number of other systems may be included. Although an aerospace example is shown, the principles of the invention may be applied to other industries, such as the automotive industry.

Apparatus and methods shown or described herein may be employed during any one or more of the stages of the manufacturing and service method 1100. For example, components or subassemblies corresponding to component and subassembly manufacturing 1108 may be fabricated or manufactured in a manner similar to components or subassemblies produced while the aircraft 1102 is in service. Also, one or more aspects of the apparatus, method, or combination thereof may be utilized during the production stages 1108 and 1110, for example, by substantially expediting assembly of or reducing the cost of an aircraft 1102. Similarly, one or more aspects of the apparatus or method realizations, or a combination thereof, may be utilized, for example and without limitation, while the aircraft 1102 is in service, e.g., maintenance and service 1116.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings.

Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. A method of testing a coupon that comprises
a first surface including a first circular channel;
a second surface opposite and parallel to the first surface,
   the second surface spaced a distance D0 from the first surface and including a second circular channel concentric with the first circular channel; and
a toroidal portion between the first circular channel and the second circular channel,
   the toroidal portion including a rectangular sectional portion,
   the first surface including a first inner region located within an inner radius R1$b$ of the first circular channel and a first outer region located outside an outer radius R1$a$ of the first circular channel,
   the second surface including a second inner region located within an inner radius R2$b$ of the second circular channel and a second outer region located outside an outer radius R2$a$ of the second circular channel,
   wherein the outer radius R1$a$ is less than the inner radius R2$b$,
the method comprising:
exerting a stress on the toroidal portion of the coupon; and
measuring deformation of the toroidal portion responsive to the stress.

2. The method of claim 1, wherein the stress is a tensile stress.

3. The method of claim 2, wherein exerting the tensile stress on the toroidal portion of the coupon includes simultaneously applying:
a first force to the first inner region in a direction perpendicular to the first surface and the second surface;
a second force to the second outer region, wherein the first force and the second force face each other and are equal in magnitude; and
no force to the first outer region and second inner region.

4. The method of claim 3, wherein the first force is applied by a first punch.

5. The method of claim 4, wherein the first punch is substantially concentrically aligned with the first circular channel and the second circular channel when the first force is applied by the first punch to the first inner region.

6. The method of claim 5, wherein the first punch contacts the first inner region without contacting the first outer region when the first force is applied by the first punch to the first inner region.

7. The method of claim 6, wherein the first punch includes a first circular circumference.

8. The method of claim 3, wherein the second force is applied by a first plate having a first circular opening.

9. The method of claim 8, wherein the first circular opening is substantially concentrically aligned with the first circular channel and the second circular channel when the second force is applied by the first plate to the second outer region.

10. The method of claim 9, wherein the first plate contacts the second outer region without contacting the second inner region.

11. The method of claim 1, wherein the stress is a compressive stress.

12. The method of claim 11, wherein exerting the compressive stress on the toroidal portion of the coupon includes simultaneously applying:
a third force to the second inner region in a direction perpendicular to the first surface and the second surface;
a fourth force to the first outer region, wherein the third force and the fourth force face each other and are equal in magnitude; and
no force to the first inner region and the second outer region.

13. The method of claim 12, wherein the third force is applied by a second punch.

14. The method of claim 13, wherein the second punch is substantially concentrically aligned with the first circular channel and the second circular channel when the third force is applied by the second punch to the second inner region.

15. The method of claim 14, wherein the second punch contacts the second inner region without contacting the second outer region when the third force is applied by the second punch to the second inner region.

16. The method of claim 13, wherein the second punch includes a second circular circumference.

17. The method of claim 12, wherein the fourth force is applied by a second plate having a second circular opening.

18. The method of claim 17, wherein the second circular opening is substantially concentrically aligned with the first circular channel and the second circular channel when the fourth force is applied by the second plate to the first outer region.

19. The method of claim 18, wherein the second plate contacts the first outer region without contacting the first inner region.

20. The method of claim 1, further comprising exposing the toroidal portion to environmental conditions.

* * * * *